(12) United States Patent
Damnjanovic et al.

(10) Patent No.: US 11,878,182 B1
(45) Date of Patent: Jan. 23, 2024

(54) HYBRID ELECTRO-PLASMONIC MODULATION OF NEURAL ACTIVITY WITH VISIBLE-LIGHT-SENSITIVE GOLD NANOTRANSDUCER INTERFACE

(71) Applicant: University of South Florida, Tampa, FL (US)

(72) Inventors: Ratka Damnjanovic, Oldsmar, FL (US); Parveen Bazard, Tampa, FL (US); Robert Dana Frisina, Tampa, FL (US); Venkat Rama Bhethanabotla, Tampa, FL (US)

(73) Assignee: University of South Florida, Tampa, FL (US)

( * ) Notice: Subject to any disclaimer, the term of this patent is extended or adjusted under 35 U.S.C. 154(b) by 345 days.

(21) Appl. No.: 17/239,389

(22) Filed: Apr. 23, 2021

Related U.S. Application Data

(60) Provisional application No. 63/014,221, filed on Apr. 23, 2020.

(51) Int. Cl.
    *A61N 5/06*     (2006.01)
    *A61N 1/36*     (2006.01)
    *B82Y 5/00*     (2011.01)

(52) U.S. Cl.
    CPC ....... *A61N 5/0622* (2013.01); *A61N 1/36164* (2013.01); *A61N 1/36167* (2013.01); *A61N 5/0601* (2013.01); *B82Y 5/00* (2013.01); *A61N 2005/0632* (2013.01); *A61N 2005/0663* (2013.01)

(58) Field of Classification Search
    CPC .............. A61N 5/0622; A61N 1/36164; A61N 1/36167; A61N 5/0601; A61N 2005/0632; A61N 2005/0663; B82Y 5/00
    See application file for complete search history.

(56) References Cited

U.S. PATENT DOCUMENTS

| 8,160,696 B2 | 4/2012 | Bendett et al. |
| 9,937,359 B1 * | 4/2018 | Bazard ................. A61N 5/0603 |

(Continued)

FOREIGN PATENT DOCUMENTS

| WO | 2019168714 A2 | 9/2019 |

OTHER PUBLICATIONS

Wang, Y. et al. Nanomaterial-Enabled Neural Stimulation. Front. Neurosci. 2016, 10, 69.

(Continued)

*Primary Examiner* — Carl H Layno
*Assistant Examiner* — Aya Ziad Bakkar
(74) *Attorney, Agent, or Firm* — Michele L. Lawson; Smith & Hopen, P.A.

(57) ABSTRACT

A method of modulating neural activity using a combination of electrical and optical stimulation transmitted via a gold nanoparticle covered nanoelectrode is presented. The combination of short-duration green visible light optical pulses with the complementary sub-threshold level electric current pulses are capable of producing action potentials in neurons. Cells were found to have a greater than a 5× survival rate using this hybrid stimulation method as compared to pure plasmonic/optical stimulation. The cell stimulation success rate was 3× greater with hybrid stimulation.

18 Claims, 8 Drawing Sheets
(8 of 8 Drawing Sheet(s) Filed in Color)

(56) References Cited

U.S. PATENT DOCUMENTS

| | | |
|---|---|---|
| 10,463,878 B2 | 11/2019 | Bazard et al. |
| 2012/0034622 A1* | 2/2012 | Ignatius .................. B82Y 5/00 435/7.2 |

OTHER PUBLICATIONS

Deisseroth, K., Optogenetics: 10 Years of Microbial Opsins in Neuroscience. Nat. Neurosci. 2015, 18, 1213-1225.

Colombo, E. et al. Nanoparticles: A Challenging Vehicle for Neural Stimulation. Front. Neurosci. 2016, 10, 105.

Marino, A. et al. Piezoelectric Nanoparticle-Assisted Wireless Neuronal Stimulation. ACS Nano 2015, 9, 7678-7689.

Johannsmeier, S. et al. "Gold nanoparticle-mediated laser stimulation causes a complex stress signal in neuronal cells." European Conference on Biomedical Optics. Optical Society of America, 2017.

Eom, K. et al. Enhanced Infrared Neural Stimulation Using Localized Surface Plasmon Resonance of Gold Nanorods. Small 2014, 10, 3853-3857.

Yong, J. et al. Gold-Nanorod-Assisted Near-Infrared Stimulation of Primary Auditory Neurons. Adv. Healthcare Mater. 2014, 3, 1862-1868.

Chen, S. et al. Near-Infrared Deep Brain Stimulation via Upconversion Nanoparticle-Mediated Optogenetics. Science 2018, 359, 679-684.

Yoo, S. et al. Photothermal Inhibition of Neural Activity with Near-Infrared-Sensitive Nanotransducers. ACS Nano 2014, 8, 8040-8049.

Li, W. et al. Remote Modulation of Neural Activities via Near-Infrared Triggered Release of Biomolecules. Biomaterials 2015, 65, 76-85.

Pappas, T. C. et al. Nanoscale Engineering of a Cellular Interface with Semiconductor Nanoparticle Films for Photoelectric Stimulation of Neurons. Nano Lett. 2007, 7), 513-519.

Duke, A. R. et al. Combined Optical and Electrical Stimulation of Neural Tissue In Vivo. J. Biomed. Opt. 2009, 14, 060501.

Zhao, Y. et al. Wireless Activation of Neurons in Brain Slices Using Nanostructured Semiconductor Photoelectrodes. Angew. Chem., Int. Ed. Engl. 2009, 48, 2407-2410.

Parameswaran, R. et al. Photoelectrochemical Modulation of Neuronal Activity with Free-standing Coaxial Silicon Nanowires. Nat. Nanotechnol. 2018, 13, 260.

Rettenmaier, A. et al. Nanosecond Laser Pulse Stimulation of Spiral Ganglion Neurons and Model Cells. Biomed. Opt. Express 2014, 5, 1014-1025.

Zhang, J. et al. Optical Detection of Brain Cell Activity Using Plasmonic Gold Nanoparticles. Nano Lett. 2009, 9, 519-524.

Shapiro, M. G. et al. Infrared Light Excites Cells by Changing Their Electrical Capacitance. Nat. Commun. 2012, 3, 736.

Wells, J. et al. Optical Stimulation of Neural Tissue In Vivo. Opt. Lett. 2005, 30, 504-506.

Nakatsuji, H. et al. Thermosensitive Ion Channel Activation in Single Neuronal Cells by Using Surface-Engineered Plasmonic Nanoparticles. Angew. Chem. Int. Ed. 2015, 54, 11725-11729.

Eom, K. et al. Theoretical Study on Gold-Nanorod-Enhanced Near-Infrared Neural Stimulation. Biophys. J. 2018, 115, 1481-1497.

Bazard, P. et al. Nanoparticle-Based Plasmonic Transduction for Modulation of Electrically Excitable Cells. Sci. Rep. 2017, 7, 7803.

Martino, N. et al. Photothermal Cellular Stimulation in Functional Bio-Polymer Interfaces. Sci. Rep. 2015, 5, 8911.

Plaksin, M. et al. Thermal Transients Excite Neurons through Universal Intramembrane Mechanoelectrical Effects. Phys. Rev. X 2018, 8, 011043.

Bec, J. M. et al. Characteristics of Laser Stimulation by Near-Infrared Pulses of Retinal and Vestibular Primary Neurons. Lasers Surg. Med. 2012, 44, 736-745.

Cayce, J. M. et al. Infrared Neural Stimulation of Primary Visual Cortex in Non-Human Primates. NeuroImage 2014, 84, 181-190.

Cayce, J. M. et al. Pulsed Infrared Light Alters Neural Activity in Rat Somatosensory Cortex In Vivo. NeuroImage 2011, 57, 155-166.

Damnjanovic, R. et al. Hybrid Electro-Plasmonic Neural Stimulation with Visible-Light-Sensitive Gold Nanoparticles. ACS Nano, Jun. 30, 2020. https://dx.doi.org/10.1021/acsnano.0c00722.

Mohapatra, S. et al. Advances in Translational Nanotechnology: Challenges and Opportunities. Applied Science. 2020, 10, 4881; doi: 10.3390/app10144881.

Carvalho-de-Souza, J. et al. "Photosensitivity of neurons enabled by cell-targeted gold nanoparticles." Neuron 86.1 (2015): 207-217.

Seyed N. et al. "Plasmonic Heating of Gold Nanoparticles for Controlling of Current Across Lipid Membranes in Modulating Neuronal Behavior Applications." European Quantum Electronics Conference. Optical Society of America, 2019.

Wenzel, G. et al. Green laser light activates the inner ear. Journal of Biomedical Optics 14(4), 044007 (Jul./Aug. 2009).

Nazari, M. et al. Plasmonic Heating of Gold Nanoparticles for Controlling of Current Across Lipid Membranes in Modulating Neuronal Behavior Applications. 2019 CLEO Europe and EQEC.

Bodelon, G. et al. Gold nanoparticles for regulation of cell function and behavior, Nano Today 13 (2017) 40-60.

Alghazali, K., et al. "Plasmonic Nanofactors as Switchable Devices to Promote or Inhibit Neuronal Activity and Function." Nanomaterials 9.7 (2019): 1029.

* cited by examiner

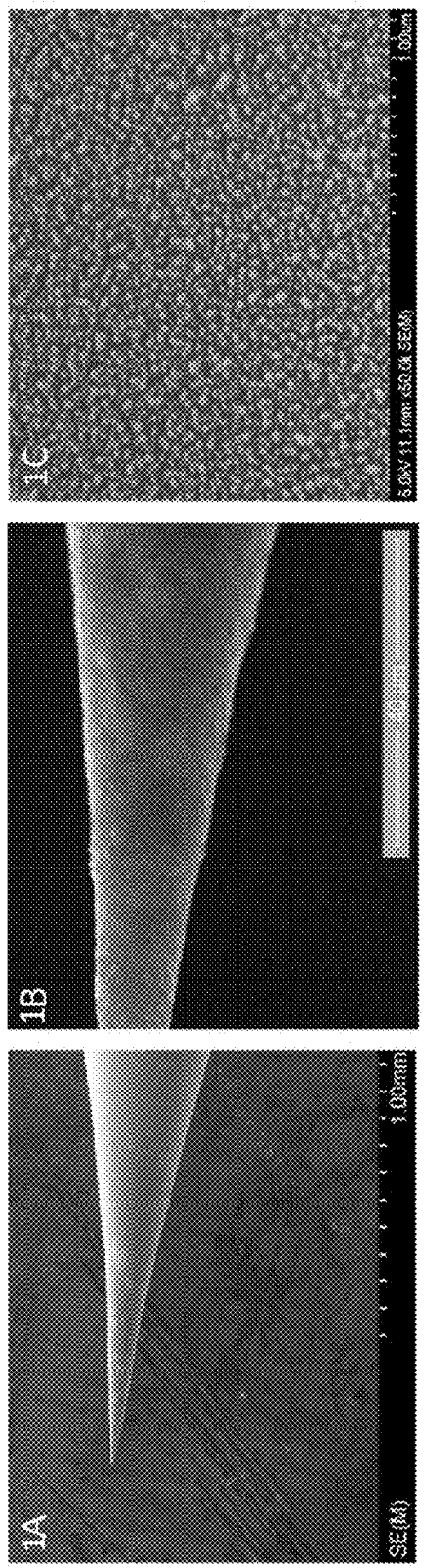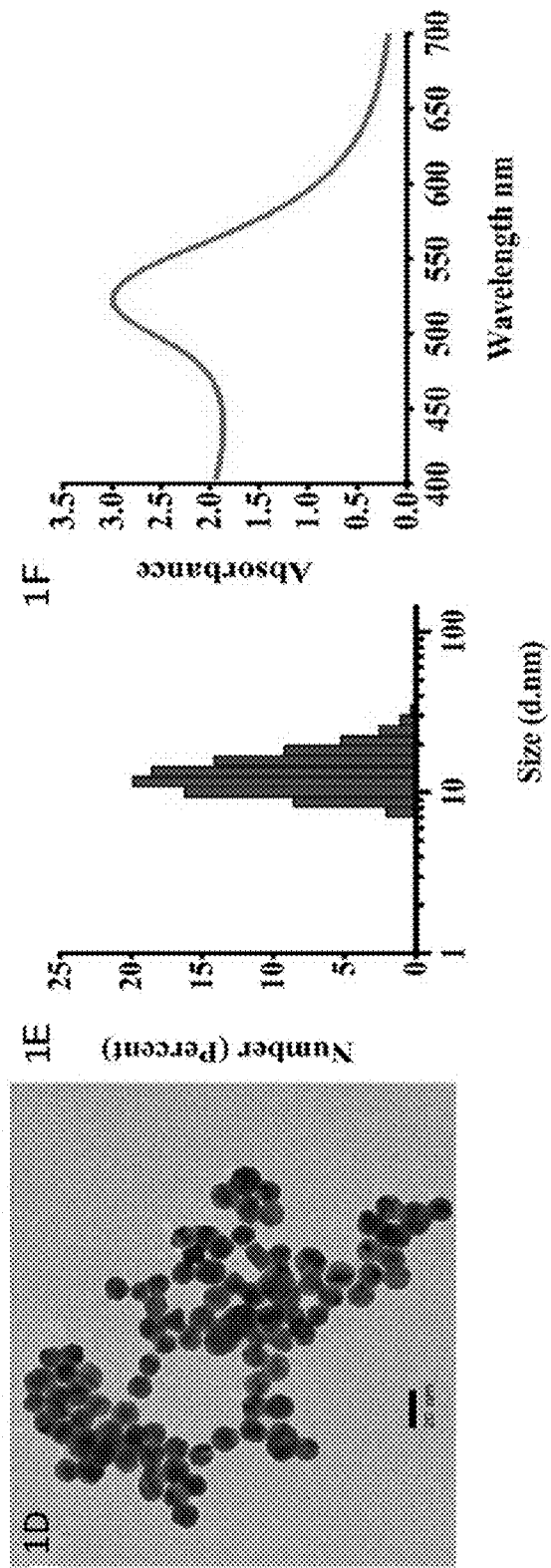
FIG. 1A-F (a)
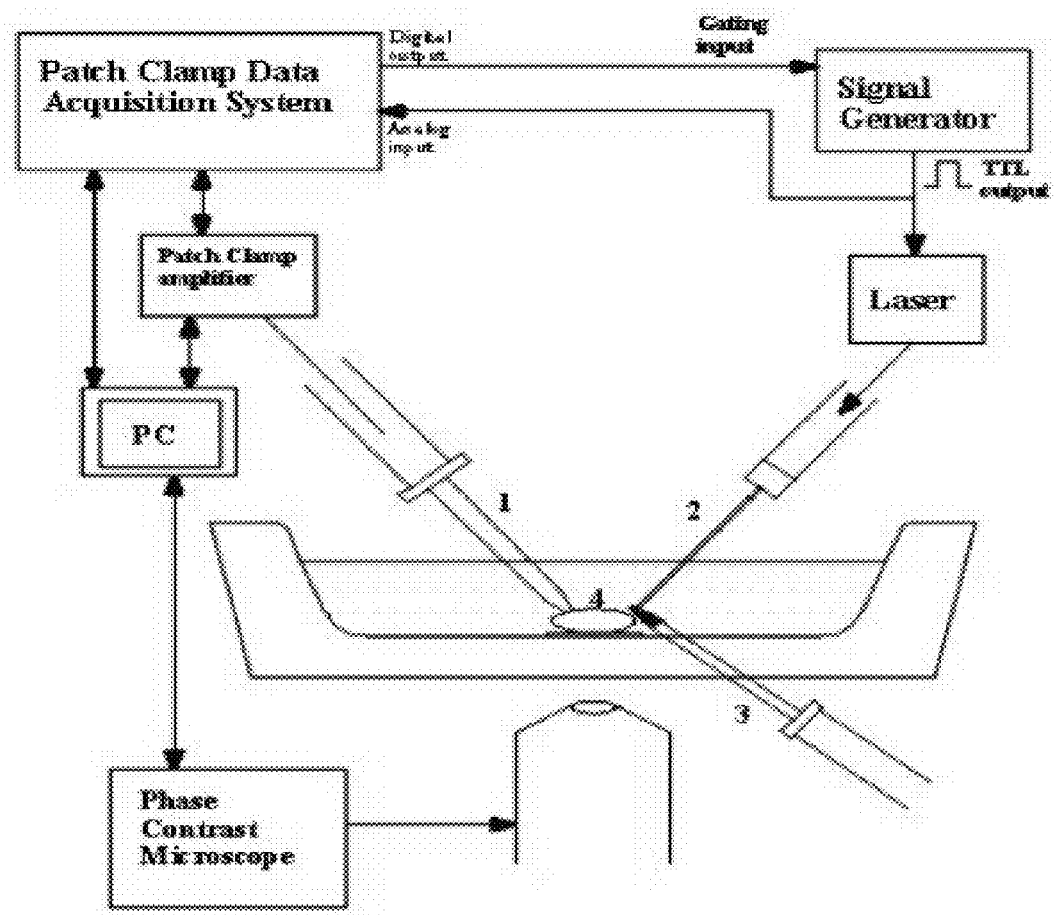
(b)
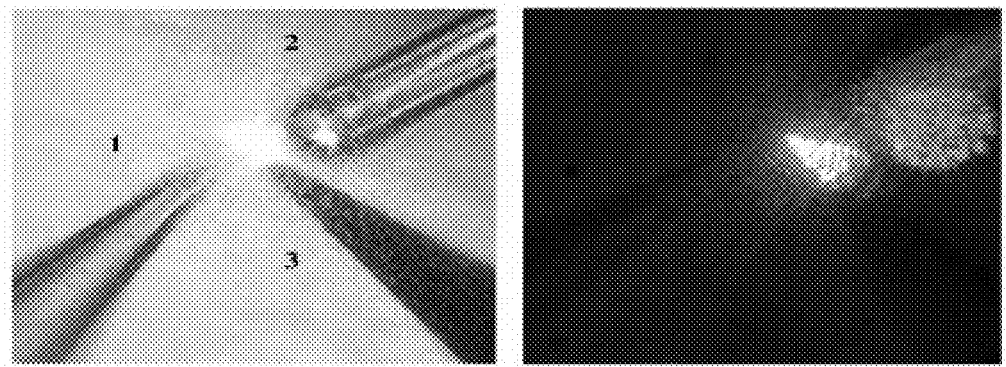
FIG. 2A-B

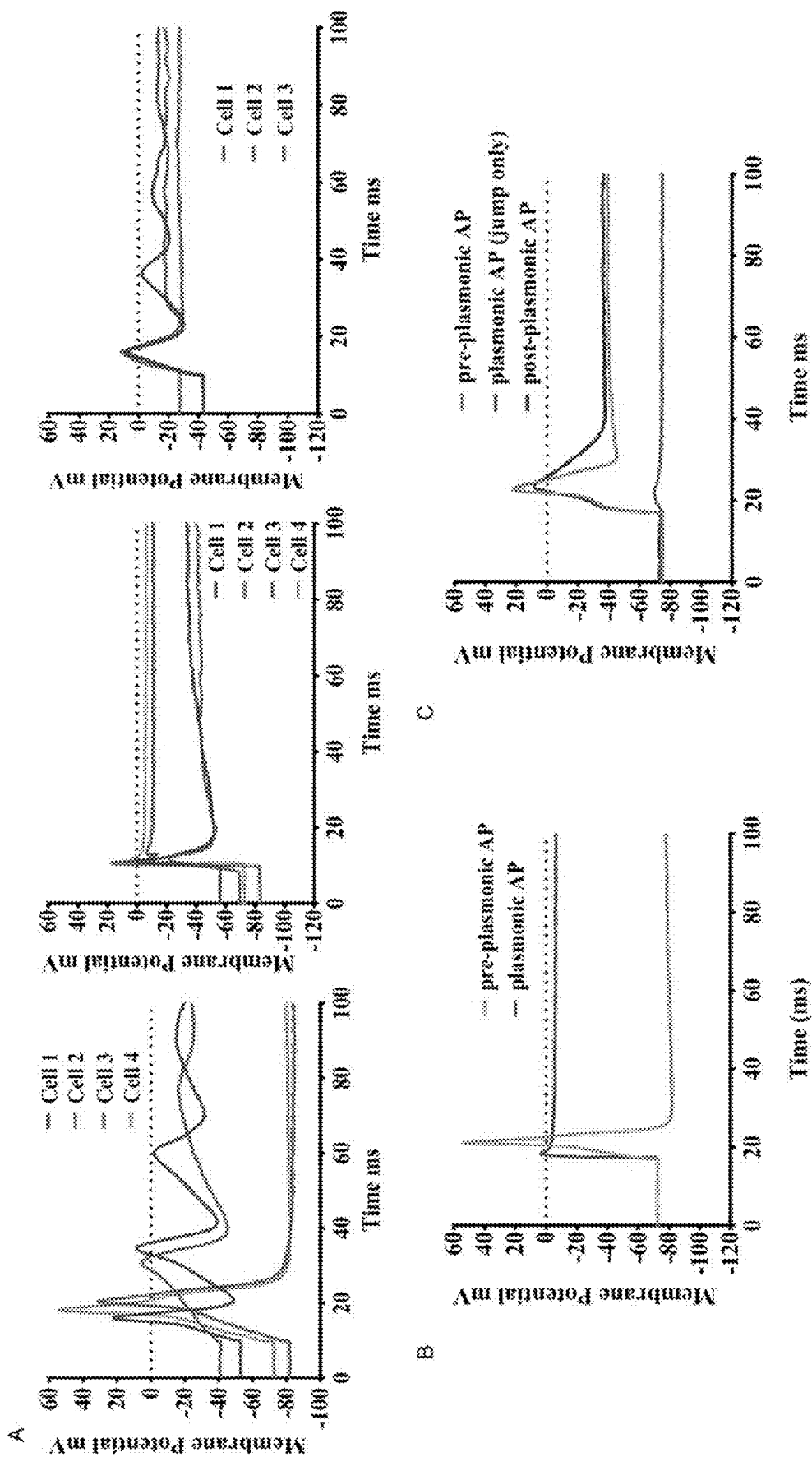
FIG. 3A-C

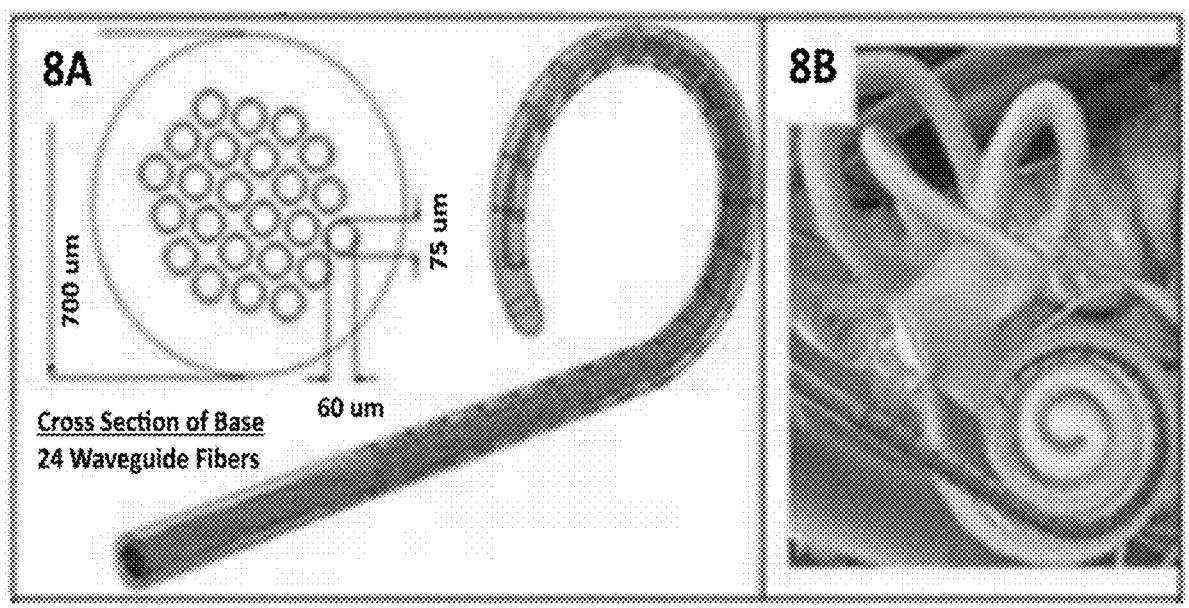
FIG. 8A-B

HYBRID ELECTRO-PLASMONIC MODULATION OF NEURAL ACTIVITY WITH VISIBLE-LIGHT-SENSITIVE GOLD NANOTRANSDUCER INTERFACE

CROSS REFERENCE TO RELATED APPLICATIONS

This application is a nonprovisional of and claims priority to U.S. Provisional Application No. 63/014,221 entitled "Hybrid Electro-Plasmonic Modulation of Neural Activity with Visible-Light-Sensitive Gold Nanotransducer Interface", filed Apr. 23, 2020, the contents of which are hereby incorporated by reference into this disclosure.

GOVERNMENTAL SUPPORT

This invention was made with government support under Grant No. P01 AG009524 awarded by the National Institutes of Health. The Government has certain rights in the invention.

FIELD OF INVENTION

This invention relates to neural stimulation. Specifically, the invention provides a method of stimulating neural cells using a hybrid electro-plasmonic approach with a visible-light-sensitive nanotransducer interface.

BACKGROUND OF THE INVENTION

Electrical stimulation, although successful at activating neural responses, tends to spread to surrounding tissues, resulting in non-specific stimulation, making it difficult to stimulate discrete neural sites. To facilitate specific point stimulation, various nanomaterial-assisted neural stimulation approaches have been reported in recent years where different localized fields are activated (electric, magnetic, thermal) employing different nanomaterials for stimulation, such as piezoelectric ultrasound waves, magnetic fields, and laser light electromagnetic waves (mainly near-infrared and infrared) optical irradiation. (Wang, Y.; Guo, L., Nanomaterial-Enabled Neural Stimulation. Front. Neurosci. 2016, 10, 69; Deisseroth, K., Optogenetics: 10 Years of Microbial Opsins in Neuroscience. Nat. Neurosci. 2015, 18, 1213-1225; Colombo, E.; Feyen, P.; Antognazza, M. R.; Lanzani, G.; Benfenati, F., Nanoparticles: A Challenging Vehicle for Neural Stimulation. Front. Neurosci. 2016, 10, 105; Carvalho-de-Souza, J. L.; Treger, J. S.; Dang, B.; Kent, S. B.; Pepperberg, D. R.; Bezanilla, F., Photosensitivity of Neurons Enabled by Cell-Targeted Gold Nanoparticles. Neuron 2015, 86, 207-217; Marino, A.; Arai, S.; Hou, Y.; Sinibaldi, E.; Pellegrino, M.; Chang, Y. T.; Mazzolai, B.; Mattoli, V.; Suzuki, M.; Ciofani, G., Piezoelectric Nanoparticle-Assisted Wireless Neuronal Stimulation. ACS Nano 2015, 9, 7678-7689; Chen, R.; Romero, G.; Christiansen, M. G.; Mohr, A.; Anikeeva, P., Wireless Magnetothermal Deep Brain Stimulation. Science 2015, 347, 1477-1480; Eom, K.; Kim, J.; Choi, J. M.; Kang, T.; Chang, J. W.; Byun, K. M.; Jun, S. B.; Kim, S. J., Enhanced Infrared Neural Stimulation Using Localized Surface Plasmon Resonance of Gold Nanorods. Small 2014, 10, 3853-3857; Yong, J.; Needham, K.; Brown, W. G.; Nayagam, B. A.; McArthur, S. L.; Yu, A.; Stoddart, P. R., Gold-Nanorod-Assisted Near-Infrared Stimulation of Primary Auditory Neurons. Adv. Healthcare Mater. 2014, 3, 1862-1868; Chen, S.; Weitemier, A. Z.; Zeng, X.; He, L.; Wang, X.; Tao, Y.; Huang, A. J. Y.; Hashimotodani, Y.; Kano, M.; Iwasaki, H.; Parajuli, L. K.; Okabe, S.; Teh, D. B. L.; All, A. H.; Tsutsui-Kimura, I.; Tanaka, K. F.; Liu, X.; McHugh, T. J., Near-Infrared Deep Brain Stimulation via Upconversion Nanoparticle-Mediated Optogenetics. Science 2018, 359, 679-684; Yoo, S.; Hong, S.; Choi, Y.; Park, J. H.; Nam, Y., Photothermal Inhibition of Neural Activity with Near-Infrared-Sensitive Nanotransducers. ACS Nano 2014, 8, 8040-8049; Li, W.; Luo, R.; Lin, X.; Jadhav, A. D.; Zhang, Z.; Yan, L.; Chan, C. Y.; Chen, X.; He, J.; Chen, C. H.; Shi, P., Remote Modulation of Neural Activities via Near-Infrared Triggered Release of Biomolecules. Biomaterials 2015, 65, 76-85; Pappas, T. C.; Wickramanyake, W. M.; Jan, E.; Motamedi, M.; Brodwick, M.; Kotov, N. A., Nanoscale Engineering of a Cellular Interface with Semiconductor Nanoparticle Films for Photoelectric Stimulation of Neurons. Nano Lett. 2007, 7), 513-519)

Optical stimulation approaches mainly rely on top-down methodology focused on recording outputs in response to a stimulation input, such as observing muscle contraction as a result of the triggered action potential (AP) response in various animal subjects. (Duke, A. R.; Cayce, J. M.; Malphrus, J. D.; Konrad, P.; Mahadevan-Jansen, A.; Jansen, E. D., Combined Optical and Electrical Stimulation of Neural Tissue In Vivo. J. Biomed. Opt. 2009, 14, 060501). More recently, there have been reports of optical stimulation performed in brain tissue slices as well as single cell stimulation of cultured neurons (dorsal root ganglion, spiral ganglion, hippocampal neurons, oocytes). (Zhao, Y.; Larimer, P.; Pressler, R. T.; Strowbridge, B. W.; Burda, C., Wireless Activation of Neurons in Brain Slices Using Nanostructured Semiconductor Photoelectrodes. Angew. Chem., Int. Ed. Engl. 2009, 48, 2407-2410; Parameswaran, R.; Carvalho-de-Souza, J. L.; Jiang, Y.; Burke, M. J.; Zimmerman, J. F.; Koehler, K.; Phillips, A. W.; Yi, J.; Adams, E. J.; Bezanilla, F., Photoelectrochemical Modulation of Neuronal Activity with Free-standing Coaxial Silicon Nanowires. Nat. Nanotechnol. 2018, 13, 260; Rettenmaier, A.; Lenarz, T.; Reuter, G., Nanosecond Laser Pulse Stimulation of Spiral Ganglion Neurons and Model Cells. Biomed. Opt. Express 2014, 5, 1014-1025; Zhang, J.; Atay, T.; Nurmikko, A. V., Optical Detection of Brain Cell Activity Using Plasmonic Gold Nanoparticles. Nano Lett. 2009, 9, 519-524; Shapiro, M. G.; Homma, K.; Villarreal, S.; Richter, C. -P.; Bezanilla, F., Infrared Light Excites Cells by Changing Their Electrical Capacitance. Nat. Commun. 2012, 3, 736). A common approach has been to use infrared (IR) light wavelengths to heat the surrounding aqueous medium sufficiently to induce fast changes in the temperature of the local surroundings, which can heat and stimulate the cell's membrane, presumably triggering membrane capacitive currents. (Shapiro, M. G.; Homma, K.; Villarreal, S.; Richter, C. -P.; Bezanilla, F., Infrared Light Excites Cells by Changing Their Electrical Capacitance. Nat. Commun. 2012, 3, 736; Wells, J.; Kao, C.; Mariappan, K.; Albea, J.; Jansen, E. D.; Konrad, P.; Mahadevan-Jansen, A., Optical Stimulation of Neural Tissue In Vivo. Opt. Lett. 2005, 30, 504-506)

Although direct heating of the bulk solution has been shown to be effective in triggering action potentials, it is an imprecise way to stimulate neurons as it heats non-specifically, and may cause cellular damage. Attempts have been made to modify the stimulation methods and utilize localized surface plasmon resonance (LSPR) fields for more target-specific heating. Nanoparticle techniques, such as functionalization, bio-conjugation and local injection or deposition of nanoparticles to the target site have been attempted. (Carvalho-de-Souza et al. 2015). For example, Parameswaran et al. demonstrated that cathodic photocurrents from single nanowires can elicit action potentials in primary rat dorsal root ganglion (DRG) neurons through a primarily atomic gold-enhanced photoelectrochemical process using coaxial p-type/intrinsic/n-type (PIN) silicone nanowires (SiNWs), where on optical stimulation with 532 nm light illumination at the neuron/PIN-SiNW interface, electrons move towards the n-type shell and holes to the p-type core, inducing a Faradaic cathodic process at the n-shell that locally depolarized the target neuron. Carvalho-de-Souza et al. conjugated Au nanoparticles with three different ligands—Ts1 neurotoxin and two antibodies (targeting TRPV1 and $P2X_3$ channel receptors respectively), and successfully bound the particles to dorsal root ganglion neurons, then stimulated the DRGs with 532 nm green laser light. Nakatsuji et al. presented a method using plasma-membrane-targeted gold nanorods (pm-AuNRs) prepared with a cationic protein/lipid complex to activate a thermosensitive cation channel, TRPV1, in intact neuronal cells by using near-infrared (NIR) light. (Nakatsuji, H.; Numata, T.; Morone, N.; Kaneko, S.; Mori, Y.; Imahori, H.; Murakami, T., Thermosensitive Ion Channel Activation in Single Neuronal Cells by Using Surface-Engineered Plasmonic Nanoparticles. *Angew. Chem. Int. Ed.* 2015, 54, 11725-11729). In this study, the highly localized photothermal heat generation, mediated by the pm-AuNRs, induced $Ca^{2+}$ influx solely by TRPV1 activation. Eom et al. conjugated Au nanorods by injection into the rat sciatic nerve using a glass pipette and then excised the nerve bundle and recorded compound nerve action potentials in response to 980 nm IR laser stimulation. (Eom, K.; Kim, J.; Choi, J. M.; Kang, T.; Chang, J. W.; Byun, K. M.; Jun, S. B.; Kim, S. J., Enhanced Infrared Neural Stimulation Using Localized Surface Plasmon Resonance of Gold Nanorods. *Small* 2014, 10, 3853-3857).

Recently, it has been shown that neural cells can be activated more efficiently by pulsed NIR light delivered to gold nanorods (GNRs) near the neural cells, but the mechanisms underlying this GNR-enhanced NIR stimulation have not been explained yet. Eom et al. proposed a model to elucidate the mechanisms by modeling the heat generated from interactions between NIR light and GNRs, the temperature-dependent ion channels (transient receptor potential vanilloid 1; TRPV1) in the neuronal membrane, and a heat-induced capacitive membrane current. Their results show that NIR pulses induce rapid temperature increases near the neural membrane triggering TRPV1-channel currents and capacitive currents. (Eom, K.; Byun, K. M.; Jun, S. B.; Kim, S. J.; Lee, J., Theoretical Study on Gold-Nanorod-Enhanced Near-Infrared Neural Stimulation. *Biophys. J.* 2018, 115, 1481-1497). Both currents collectively increase the generator potential eliciting an action potential, and the stimulus conditions determine which source will be the dominant mechanism, such as the laser pulse duration or the TRPV1 channel density. They concluded that, although the TRPV1 mechanism dominates in most cases, the capacitive current has a greater contribution when a very short laser pulse is used for neural cells with relatively low TRPV1 channel densities.

Yoo et al. performed coating of Au nanorods with polyethylene glycol (PEG) to assist binding to the cell membrane, and then invoked inhibition in the rat hippocampal tissue using a 785 nm NIR laser. (Yoo, S.; Hong, S.; Choi, Y.; Park, J. H.; Nam, Y., Photothermal Inhibition of Neural Activity with Near-Infrared-Sensitive Nanotransducers. *ACS Nano* 2014, 8, 8040-8049). Li et al. utilized photosensitive hydrogels embedded with polypyrrole (PPy) nanoparticles to release biomolecule transmitters (glutamate & DNQX), and then used 980 nm IR laser light to excite hippocampal neurons in-vitro when glutamate was released, and to inhibit responses from the rat visual cortex in-vivo when DNQX was released. (Li, W.; Luo, R.; Lin, X.; Jadhav, A. D.; Zhang, Z.; Yan, L.; Chan, C. Y.; Chen, X.; He, J.; Chen, C. H.; Shi, P., Remote Modulation of Neural Activities via Near-Infrared Triggered Release of Biomolecules. *Biomaterials* 2015, 65, 76-85). Yong et al. incubated primary auditory neurons with silica-coated Au nanorods overnight and used 780 nm NIR laser to excite the neurons. (Yong, J.; Needham, K.; Brown, W. G.; Nayagam, B. A.; McArthur, S. L.; Yu, A.; Stoddart, P. R., Gold-Nanorod-Assisted Near-Infrared Stimulation of Primary Auditory Neurons. *Adv. Healthcare Mater.* 2014, 3, 1862-1868)

Cochlear implants are generally comprised of a set of tiny metal wire electrodes that are placed into the cochlea—the part of the inner ear used for hearing. The different electrodes stimulate different parts of the inner ear and auditory nerve fiber, the nerve cells that connect the inner ear with the parts of the brain used for hearing, via current pulses based on sound frequencies. The inner ear sensory epithelium is organized like the keys on a piano, high frequencies towards the base of the cochlea and low frequencies towards the apex of the cochlea, thus, mimicking the tonotopic or spatiotopic organization of the cochlea and auditory system. The spatial selectivity of cochlear implants is poor due to the spread of electrical currents, making it is difficult to stimulate discrete auditory neurons according to specific sound frequencies, as occurs in normal hearing. Specifically, the processing of music sounds to the desired perception of cochlear implant users remains a significant problem to be addressed because, normally, music has many frequencies at various volume levels. The same happens with human speech when there is a background noise.

The external component of a cochlear implant contains a microphone, a speech processor and a transmitter. The microphone picks up acoustic sounds and sends it to the speech processor. The processor analyzes and digitizes the signal before sending it to the transmitter. The transmitter then codes the signals and sends them to the implanted receiver via the magnetic coupling. The receiver collects the signals from the transmitter and converts them to electrical pulses. It then dispatches the pulses to the electrodes that have been inserted deeply into the inner ear. These electrodes directly stimulate the auditory nerve throughout a portion of the cochlea and the brain then interprets these signals as sound.

Biomedical prosthetics utilizing electrical stimulation have limited, effective spatial resolution due to spread of electrical currents to surrounding tissue, causing nonselective stimulation. As such, precise spatial resolution is not possible for traditional neural prosthetic devices, such as cochlear implants. Recently, to facilitate specific point stimulation, various nanomaterial-assisted neural stimulation approaches have been reported where different localized fields are activated. For example, infrared stimulation has been shown to excite neurons. However, infrared stimulation has its own drawbacks, as it may cause collateral heating of surrounding tissue. In previous work, the inventors employed a plasmonic method for stimulation of an electrically excitable neuroblastoma cell line which used visible green light and gold nanoparticle-coated microelectrodes for plasmonic modulation of SH-SY5Y neuroblastoma cells. Unfortunately, the study exhibited limited success with detrimental effects on cell membranes with higher levels of pure optical stimulation.

A common theme for these studies is that they employ various modifications of nano-neural interfaces to achieve optical stimulation. The major limitation with these techniques is that they have issues regarding unwanted toxicity, biocompatibility and repeatability. For instance, excessive heating by IR lasers to excite neurons can damage healthy tissues. In light of the shortcomings of the prior art, there is a need to find more suitable ways for conversion into new neural prosthetics that would minimize cellular and surrounding tissue damage.

SUMMARY OF INVENTION

The inventors have developed a novel next-generation hybrid electro-plasmonic stimulation system for spatially and temporally precise neural excitation to address the deficiencies of the prior art. The hybrid electro-plasmonic stimulation method was tested in a whole-cell patch-clamp configuration to elicit electrical responses in primary trigeminal neurons. The inventors found that hybrid stimulation, using both electrical and visible light pulses, of trigeminal neurons demonstrated various combinations of sub-threshold levels of electrical and short-duration visible light (532 nm) pulses can successfully modulate neural firing patterns. Trigeminal neurons were co-stimulated in-vitro in a whole-cell patch-clamp configuration with sub-threshold-level short duration electrical and visible light pulses (1-10 ms, 1-5 V, 10 Hz) aimed at a gold-nanoparticle coated nanoelectrode placed adjacent to a neuron. The electrical stimulus amplitude required to evoke action potentials is significantly reduced (up to 40%) when a plasmonic stimulus (1-5 V, 1-5 ms pulse) is added, compared to electrical stimulation alone. Membrane action potentials were recorded with a higher success rate and better post-stimulation cell recovery than with pure optical stimulation. Neuron cell survival and viability after hybrid stimulation is superior to that of pure optical stimulation (72% vs. 13%). The reduction of current required to trigger action potentials, and the finding that cells stay healthy after repeated exposure to hybrid stimulation, contribute to the development of tunable neural stimulation systems. Such systems include, but are not limited to, prosthetic devices such as cochlear implants that offer improved frequency modulation and specificity by more selective, focused and tunable activation of auditory neurons along the cochlear frequency axis.

In an embodiment, a method of modulating neural activity in at least one neuron is presented. The method comprises delivering an electrical pulse, lasting between about 1-10 ms, to the at least one neuron using a nanoelectrode coated in an array of gold nanoparticles and positioned adjacent to the at least one neuron and delivering an optical pulse, lasting between about 1-5 ms, to the at least one neuron wherein at least one action potential of the at least one neuron is stimulated or inhibited by the application of the optical pulse and the electrical pulse to modulate the neural activity.

The method may further comprise delivering subsequent pulses in an alternating pattern of one electrical pulse and one optical pulse to the at least one neuron. Alternatively, the method may further comprise delivering subsequent optical and electrical pulses simultaneously.

The method may further comprise adjusting variables comprising sequence, lead and lag time, intensity thresholds, duration, or a combination thereof to fine-tune the stimulation or inhibition of the at least one action potential of the at least one neuron.

The time between the electrical pulse and the optical pulse may be less than 2 ms. The electrical pulses may be delivered at a sub-threshold level.

The array of gold nanoparticles may be configured to produce plasmonic heating when excited by a wavelength of light near their surface plasmon resonance peak. The wavelength of light may be between about 380 nm to about 800 nm. In some embodiments, the wavelength of light is about 532 nm.

In another embodiment, a method of stimulating or inhibiting an action potential in at least one nerve cell is presented. The method comprising positioning a gold nanoparticles-coated nanoelectrode adjacent to the at least one nerve cell; delivering an electrical pulse, lasting between about 1 to 10 ms, to the at least one nerve cell; delivering an optical pulse, lasting between about 1 to 5 ms, to the at least one nerve cell; and wherein the action potential of the at least one nerve cell is stimulated or inhibited by the application of the optical pulse and the electrical pulse. The electrical pulses may be delivered at a sub-threshold level.

The method may further comprise delivering subsequent pulses in an alternating pattern of one electrical pulse and one optical pulse wherein time between the electrical pulse and the optical pulse is less than 2 ms. Alternatively, the method may further comprise delivering the optical pulse and the electrical pulse simultaneously.

The method may further comprise adjusting variables comprising sequence, lead and lag time, intensity thresholds, duration, or a combination thereof to fine-tune the stimulation or inhibition of the action potential of the at least one nerve cell.

The gold nanoparticles may be configured to produce plasmonic heating when excited by a wavelength of light near their surface plasmon resonance peak.

The wavelength of light may be between about 380 nm to about 800 nm. In some embodiments, the wavelength of light is about 532 nm.

In a further embodiment, a method of stimulating multiple action potentials in a nerve cell is presented. The method comprises positioning a gold nanoparticles-coated nanoelectrode adjacent to the at least one nerve cell and delivering alternating optical and sub-threshold level electrical pulses to the at least one nerve cell. The optical pulses may have a pulse width between about 1 to 5 ms while the electrical pulses may have a pulse width of between about 1 to 10 ms. The time period between each of the optical and each of the electrical pulses may be less than about 2 ms.

The method may further comprise adjusting variables comprising sequence, lead and lag time, intensity thresholds, duration, or a combination thereof to fine-tune the stimulation of the multiple action potentials of the at least one nerve cell.

The gold nanoparticles are configured to produce plasmonic heating when excited by a wavelength of light near their surface plasmon resonance peak.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIGS. 1A-F are a series of images depicting characteristics of the nanoplasmonic microelectrode. (A, B and C)

Figure 4:
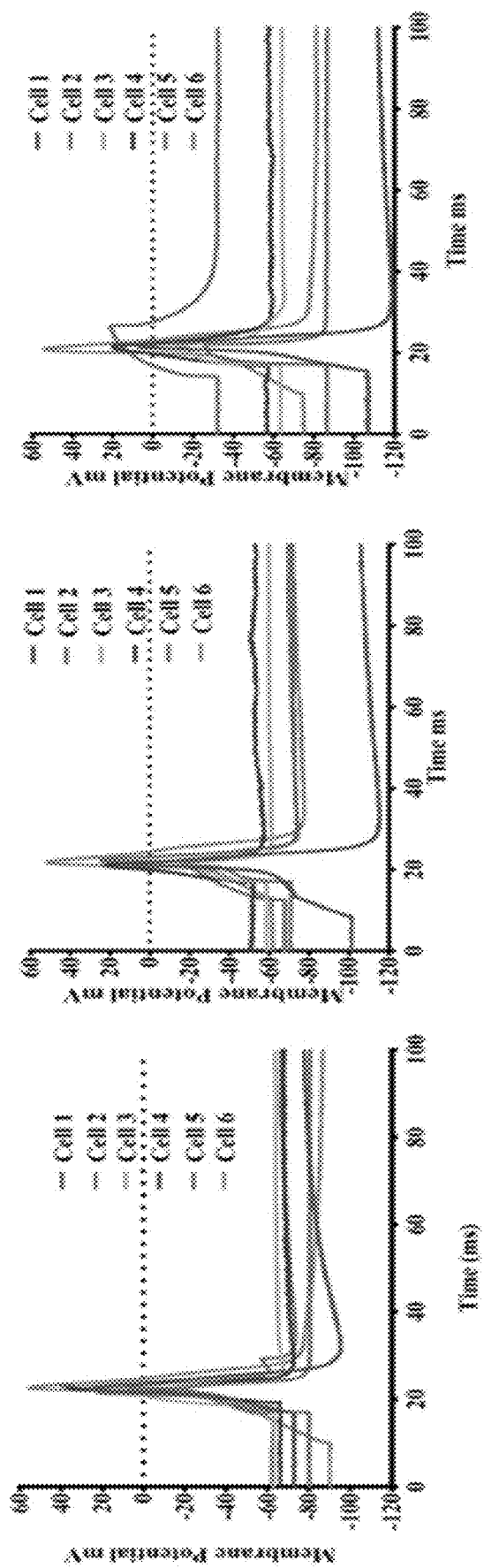

SEM images of the microelectrode, whose tip was coated with ~20 nm diameter colloidal gold nanoparticles (AuNPs). (D) TEM image of the AuNPs suspension, which was synthesized using a liquid phase method by adding 2-3 ml of a 1% solution of trisodium citrate to a boiling $HAuCl_4.3H_2O$ solution, under continuous stirring, and boiled until it turned maroon red in color, indicating the presence of AuNPs. (E) Particle size distribution histogram by number (percent) of the synthesized AuNPs, determined using Zetasizer particle counter. (F) LSPR absorption spectrum of the AuNPs, with a maximum peak value around the 520 nm wavelength, determined using Perkin Elmer Lambda 35 UV/Vis spectrophotometer (190-1100 nm wavelength range, 0.5-4 nm variable bandwidth range) to obtain the UV/Vis absorption spectra of the AuNPs solution.

FIGS. 2A-B are a series of images depicting schematic and digital pictures of the experimental patch-clamp setup. (A) Whole cell patch-clamp technique used in conjunction with an Axopatch 700B Multiclamp amplifier connected to a patch pipette filled with an intracellular solution (ICS), known as the measuring electrode (1), paired with Digidata 1440A data acquisition interface (Molecular Devices) and pCLAMP-9 software (Axon Instruments, Union City, CA, USA). Extracellular solution (ECS) was used to flood the cells (4) in the petri dish. A 50 μm inside diameter optical fiber (2) was used to focus a 532 nm green laser light onto the surface of the Au-nanoparticles (AuNPs) coated microelectrode tip (3). The AuNPs coated microelectrode was placed near the cell's surface (~2 μm). For the hybrid stimulation, an electrical stimulus was added via the patch-clamp electrode (1), in addition to the optical plasmonic stimulation generated by the laser beam (2) from the optical fiber (ThorLabs) shining onto the tip of the AuNPs coated microelectrode (3). Neural responses were recorded using the patch-clamp electrode (1). (B) Digital micrographs of the experimental patch-clamp setup when illuminated by the laser beam, inducing the plasmonic effect at the AuNPs coated microelectrode tip, as seen inside the petri dish under 5× (left) and 20× (right) magnifications.

FIGS. 3A-C are a series of graphs depicting plasmonic stimulation of primary mouse trigeminal neurons—Whole Cell Current Clamp Recordings. Current-clamp recordings of the membrane potential (mV) in trigeminal neurons elicited by shining green laser light (532 nm) at 100 mW power and 5 ms pulse duration onto the surface of an AuNPs-coated micropipette positioned ~2 μm from the cell. (A) Four representative cells excited by plasmonic neural stimulation. Left: Electrical stimulation APs (pre-plasmonic) recorded when cells were stimulated with electric current pulses (150-300 pA, 300 ms)—control condition. Middle: Plasmonic stimulation APs recorded when cells were stimulated for 1-5 ms by green laser pulses (75-120 mW laser power). The pure optical (plasmonic) APs were smaller in magnitude compared to the pure electrical (pre-plasmonic) APs. Right: Electrical stimulation APs (post-plasmonic) recorded when cells were stimulated with electric current pulses of the same magnitude as in the pre-plasmonic electrical stimulation (min 150-300 pA, 300 ms). These post-plasmonic APs were recorded with significantly smaller amplitudes than the pre-plasmonic APs. One of the cells did not survive the plasmonic stimulation, therefore it could not produce a post-plasmonic electrical AP. (B) Type 1: Typical plasmonic stimulation AP response of trigeminal neurons in a whole-cell current-clamp recording where the cell is irresponsive post-plasmonic optical stimulation. Majority of plasmonic stimulation attempts (approximately 80%) result in this type of AP response. This was likely related to cell membrane damage due to plasmonic exposure, manifested in the premature termination or leveling out of the AP response into a termination peak immediately after the depolarization phase, with no evident repolarization. In those terminated cells, the post-plasmonic electrical stimulation AP response was often not possible, as the cell's membrane damage led to no physiological response. (C) Type 2: The second most typical plasmonic stimulation AP response of trigeminal neurons in a whole-cell current-clamp recording where the cell is only partially responsive to optical stimulation. Weak membrane potential shift (10-20 mV jump) occurred, not a complete AP, or the cell was completely irresponsive to the plasmonic stimulus following a successful pre-plasmonic electrical stimulation AP. In those irresponsive cells, the post-plasmonic electrical stimulation AP response had slightly smaller amplitude, compared to the pre-plasmonic electrical stimulation AP response, and it lacked repolarization acuity.

FIG. 4 is a series of graphs depicting hybrid Electroplasmonic stimulation results—Whole Cell Current Clamp Recordings. Membrane APs of trigeminal neurons subjected to an electro-plasmonic (hybrid) stimulus in a whole-cell current-clamp recording for six different trigeminal neurons. Left: Electrical stimulation APs (pre-hybrid) recorded when cells were stimulated with electric current pulses, (min 150 pA, 5 ms)—control conditions. Middle: Electro-plasmonic (hybrid) stimulation APs recorded when the cells (N=6) were stimulated with the combined 1-5 ms, 532 nm green laser pulses and sub-threshold electric current pulses at reduced levels. When short-duration laser pulses (1-5 ms) were superimposed with electric current pulses, APs were reliably recorded from trigeminal neurons. Peak responses recorded with hybrid stimulation were higher than pure optical stimulation (FIG. 3A) by 10 to 20 mV on an average. Right: Post-hybrid electrical stimulation recordings when cells were stimulated with electric current pulses of the same magnitude as in pre-hybrid stimulation. Cells made consistently similar AP responses as the original values observed from the initial electrical (pre-hybrid) stimulation.

FIGS. 5A-E are a series of images depicting comparison of Plasmonic vs. Hybrid stimulation results of primary mouse trigeminal neurons—Whole Cell Current Clamp Recordings. (A) Mean plasmonic electrophysiology AP responses (N=4). Left: Pre-plasmonic electrical AP responses. Middle: Plasmonic APs response. Right: Post-plasmonic electrical APs response. (B) Mean hybrid (electro-plasmonic) AP responses (N=6). Left: Pre-hybrid electrical AP responses. Middle: Hybrid (electrical+optical) AP responses. Right: Post-hybrid electrical AP responses. (C) Mean input current reduction (% pA) as observed in (N=12) trigeminal cells when stimulated with hybrid electro-plasmonic stimulation vs. pure electrical current stimulation. The current reduction is 38±2%. (D) Plasmonic vs. hybrid stimulation success rate. Success rate is defined as: ratio of number of successful pure optical (or hybrid) stimulation APs vs. the total number of cells stimulated with optical (or hybrid) stimulation respectively. Observed AP success rates were 26% (N=23) for plasmonic vs. 83% (N=29) for hybrid stimulation, for cells that previously produced electrically stimulated baseline APs. The hybrid stimulation success rate is an order of magnitude >3 as compared to the plasmonic stimulation success rate. (E) Plasmonic vs. hybrid survival rate. Observed neuron survival rates were 13% (N=23) of trigeminal neurons after plasmonic stimulation vs. 72% (N=29) of trigeminal neurons after hybrid stimulation. The hybrid stimulated trigeminal neurons' survival rate is an order of magnitude >5.5 compared to the plasmonic stimulated trigeminal neurons survival rate.

FIGS. 6A-C are a series of images depicting optimization of hybrid stimulation opto-electric parameters. (A) Lead and lag time effects of electrical vs. plasmonic pulses for our hybrid electro-plasmonic stimulation paradigm. Electro-plasmonic hybrid stimulation (5 ms; 75-120 mW, 532 nm, 5 ms) pulses were applied at a sub-threshold electrical input current. The shift in membrane potential indicates that a lead or lag time greater than 1.4 ms, of either electrical or optical pulse in reference to each other, did not produce standard neural stimulation AP responses. Optical lead of up to 0.6 ms before electrical, as well as electrical lead of up to 1.4 ms before optical, both produced good hybrid APs. (B) At a fixed optical pulse duration (1 ms), hybrid sub-threshold electrical stimulation was varied from 1 to 5 ms, where the electrical pulse leads the optical by 0.7 ms in time of initiation. AP peak responses increased as the sub-threshold electrical pulse duration increased, with pulse duration of 3-5 ms being the optimal for getting full AP response from the neuron. The difference (delta) between the AP peak value and base value (first minima after peak) increased with the pulse duration increase, where the increase is greater when the pulse durations exceeds 3 ms, due to the increase in the AP peak values as well as the increase in the hyperpolarization minima. (C) Multiple APs recorded for hybrid electro-plasmonic stimulation. The reduction of current required to trigger APs with hybrid stimulation was up to 40% (FIG. 5C), and cells stayed healthy longer after repeated exposure to hybrid stimulation compared to pure plasmonic stimulation. Insets of part (C) (i, ii, iii, and iv) show the separate traces of multiple APs individually for better visibility, as follows: (i) Pre-hybrid electrically evoked multiple APs (380 pA threshold); (ii) Pre-hybrid electrically evoked shifts (200 pA); (iii) Hybrid stimulation APs (250 pA, 35% below threshold); (iv) Post-hybrid electrically evoked APs.

Figure 7:
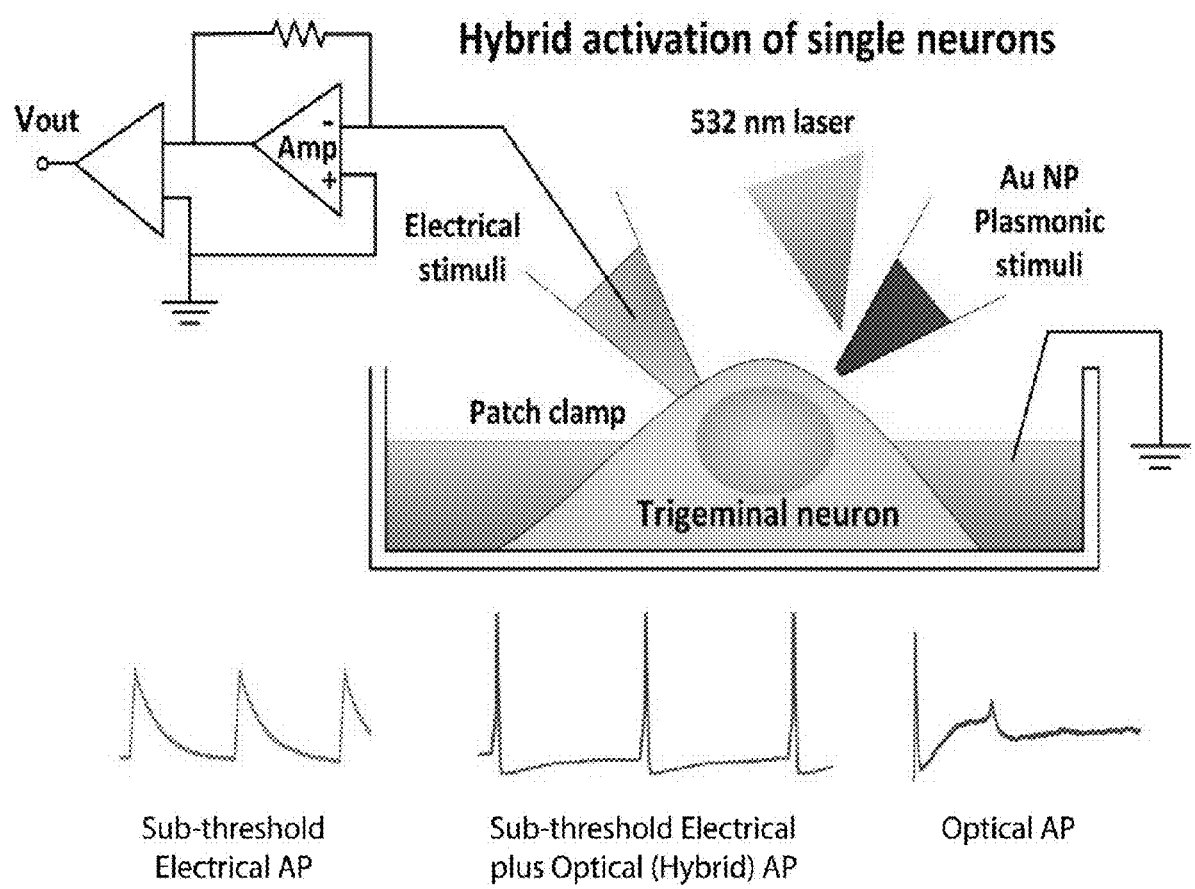

FIG. 7 is an image depicting hybrid activation of single neurons using short duration (1-5 ms) sub-threshold electrical and optical pulses applied repeatedly. It shows that the output traces from the pure sub-threshold electrical (left bottom) and the pure short-duration plasmonic (right bottom) stimulation are inferior compared to the hybrid (middle) stimulation output when those two input stimuli are combined together.

FIGS. 8A-B are a series of images depicting a new generation cochlear implant. (A) cross section at the base of the array; (B) digital model of human cochlea with the new generation electrode overlaid, as if being inserted.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

All numerical designations, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined. As used herein, the term "about" refers to ±10%.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise. For example, the term "a nanoparticle" includes a plurality of nanoparticles, including mixtures thereof.

As used herein, the term "comprising" is intended to mean that the products, compositions and methods include the referenced components or steps, but not excluding others. "Consisting essentially of" when used to define products, compositions and methods, shall mean excluding other components or steps of any essential significance. "Consisting of" shall mean excluding more than trace elements of other components or steps.

"Nanoparticle" as used herein refers to a microscopic particle having at least one dimension that is less than 100 nm. Nanoparticles used herein can be metallic and have a diameter of about 20 nm or less. Metallic nanoparticles used herein include, but are not limited to, silver, gold, copper, aluminum, palladium, and alloys thereof including bimetallic nanoparticles. Alloy composition, size of the nanoparticle, shape of the nanoparticle (cubic, spherical, rod-like, etc.) are some parameters which allow for tuning the wavelength at which plasmonic phenomena occurs in these nanoparticles. In an embodiment, the nanoparticles are gold nanoparticles and have a diameter of about 20 nm as the mean value on the particle size distribution curve (determined using Zetasizer particle counter). The particle size distribution curve is centered around the 15+/−5 nm particles size range, but there are some nanoparticles in the sample that are smaller and/or larger than this, which fall outside the peak range, therefore making the applicable particle size distribution range wider. In an embodiment, the size range may be between about 7-35 nm, with the great majority of particles (95%) being 10-30 nm particle size diameter. In some embodiments, the size range of the nanoparticles is about 20+/−10 nm, In some embodiments, 20 nm is the nominal. "Plasmonic nanoparticle", as used herein, refers to a metal nanoparticle that is highly efficient at absorbing and releasing the light as scattered light or as heat, depending upon the nanoparticle properties (shape, size, composition, etc.).

"Tuning" as used herein refers to changing the size, shape, surface chemistry or aggregation state of a nanoparticle in order to optimize the optical and electronic properties of the nanoparticle to a particular application. The plasmonic peak can be tuned to any wavelength by a suitable design of the nanoparticles as discussed in U.S. Pat. No. 9,005,890, herein incorporated in its entirety by reference.

"Surface plasmon" or "surface plasmon resonance" as used herein refers to resonant oscillations of oscillating electric fields of a ray of light propagating near a colloidal nanoparticle that interact with the free electrons thus causing an oscillation of electron charge that is in resonance with the frequency of the incident light electro-magnetic wave, including, but not limited to, the visible light wavelength.

"Nanoelectrode" as used herein refers to a microelectrode coated with metallic nanoparticles. In some embodiments, the metallic nanoparticles are gold and the microelectrode is a glass pipette.

"Visible wavelength light" refers to light having wavelengths between about 400 nm to about 800 nm. The wavelength of the utilized light is dependent upon the surface plasmon resonance (SPR) peak of the nanoparticle. The composition of the nanoparticle, as well as its size and shape, will, in part, define the SPR peak of the nanoparticle. The visible wavelength light used is dependent on the SPR of the nanoparticle. For example, in some embodiments where spherical 20 nm diameter gold nanoparticles are used, the wavelength of the light used is about 532 nm, to correspond to the SPR absorption spectrum of the gold nanoparticles, which is around 520 nm. While the invention is discussed herein as using the visible light range (380 nm to 800 nm), plasmonic phenomena can be evoked in the ultraviolet and in the infrared range as well (below 380 nm and above 800 nm). For example, gold nanorods can be tuned to have plasmonic peaks in the infrared range (900 to 1200 nm, for example) and such light can be used in the invention herein as well. However, it should be noted that ultraviolet (UV) and/or infrared (IR) light may damage the cells, hence very low intensity may be necessary.

"Adjacent" as used herein when referring to the positioning of the nanoelectrode to the cell, is defined as the distance between the nanoelectrode and the cell being on the order of varying only by a few microns. This distance is dependent on the power of the visible light or electric current used. As the power of the light or electric current increases, as does the distance between the nanoelectrode and the cell. A local rise in temperature decreases with an increase in distance away from the nanoelectrode. For example, the term "adjacent" is meant to cover distances of 0 (meaning the nanoelectrode is touching the cell) up to a distance of 6 µm from the cell. It is preferable that the nanoelectrode is as close as possible to the cell without disturbing the cell. In some embodiments, the nanoelectrode is positioned less than or equal to 2 µm from the cell. In some embodiments in which a green light laser emitting light at 532 nm is used, the nanoelectrode is placed 2 µm from the cell.

"Pulse" as used herein refers to the amount of time the energy source is emitting light for optical pulses and to a change in voltage or current intensity that lasts for a short duration of time for an electrical pulse. In order to fire action potentials, a pulse width (individual pulse duration) of between about 1-5 ms was used for optical pulses while a pulse width of between about 1-10 ms was used for electrical pulses. The pulse width for optical pulses can be correlated to the shape/size of the nanoparticles as well as the laser wavelength/power. Long duration electrical input of up to 100 ms, 200 ms or 300 ms duration (including all intervening amounts) are contemplated in the invention herein and have produced a satisfactory outcome. In some embodiments, an electrical pulse of less than 5 ms with pulsing the signal every 50 ms is used. In some embodiments, the sub-threshold electrical pulse duration was between 3-5 ms while keeping the optical pulse duration fixed at 1 ms and the electrical pulse lead time fixed to 0.7 ms before optical pulse.

The time period between each of the optical and electrical pulse (within one pair of a hybrid pulse) may be up to 2 ms, or in some embodiments, optimally less than 1.4 ms lead or lag time. The time period between each of the optical and each of the electrical pulses, meaning optical to optical and electrical to electrical, which is equivalent to the time between each of the hybrid pulse pairs, can be between about 10 ms to about 100 ms, with the optimal being about a 50 ms repetition interval.

"Hybrid stimulation" as used herein refers to a combination of optical (plasmonic) and electrical stimulation. Use of optical stimulation in conjunction with electrical stimulation allows for sub-threshold levels of electrical stimulation to be used. "Hybrid stimulation" is used interchangeably with "electro-plasmonic stimulation" and "electro-optical stimulation".

"Sub-threshold" as used herein with respect to electrical stimulation refers to levels of electrical stimulation below a 380 pA threshold, preferably below a 300 pA threshold.

"Electrically active biological cells" or "electrically excitable biological cells" as used herein includes nerve cells, cardiomyocytes, non-cardiac muscle cells, or retinal cells.

"Nerve cell", "neuron", and "neural cell" are used interchangeably herein to refer to specialized cells capable of generating electrical signals that can be transmitted throughout the body.

The inventors used an Au nanoelectrode (AuNPs-coated quartz micropipette), which did not need any bio-conjugation or surface modifications of the nano-neural interface to achieve neural excitation. This nanoelectrode was characterized and validated for generation of plasmonic responses in the inventors' previous work, herein incorporated by reference, by stimulating two different types of cells, the SH-SY5Y human neuroblastoma cell line that has characteristics of neurons, and neonatal cardiomyocytes. (Bazard, P.; Frisina, R. D.; Walton, J. P.; Bhethanabotla, V. R., Nanoparticle-Based Plasmonic Transduction for Modulation of Electrically Excitable Cells. *Sci. Rep.* 2017, 7, 7803). Here, the inventors go further by stimulating primary mouse trigeminal neurons to determine whether electro-plasmonic co-stimulation at the subthreshold level could modulate single cell neural activity of primary neurons, and more specifically trigeminal neurons.

The inventors evaluated how visible green light (532 nm, 1-5 ms pulses) could be used to stimulate primary neurons in conjunction with reduced levels of electrical stimulation. As shown previously, there was success with pure optical stimulation, but a minority of cells responded to the optical stimuli alone, and detrimental effects were generally observed on cells with higher levels of pure optical stimulation. (Bazard, P. et al. 2017). To overcome these shortcomings, the inventors used optical stimulation in conjunction with sub-threshold electrical stimuli, to consistently activate primary neurons and for improved success rates, repeatability & reproducibility. These findings serve as an initial in-vitro proof of concept for optical plasmonic stimulation of primary neurons, and more specifically trigeminal neurons, using the localized surface plasmon resonance (LSPR) phenomena.

The inventors illuminated the AuNPs-coated nanoelectrode, positioned adjacent to the neuron (within 2 μm), with a 532 nm green laser light. The inventors have expanded on employment of hybrid electro-plasmonic stimulation to elicit action potential (AP) responses in primary trigeminal neurons. The inventors also showed how various combinations of pulse durations, through repetitive bursts of electrical and plasmonic pulses at the subthreshold level, modulate neural firing patterns in primary neurons to achieve cellular AP responses with improved firing success rates, survival rates and repeatability, while significantly reducing the negative side effects, such as the overheating of surrounding tissue as with IR laser light, or the poor specificity shown with electrical stimulation alone.

The inventors chose the trigeminal nerve for culturing neurons due to its wide array of functions. The trigeminal nerve is the fifth cranial nerve and the principle sensory nerve of the head that innervates the nasal cavity, paranasal sinuses, oral mucosa and the skin of the face, as well as the cerebral arteries and the dura mater. As such, the trigeminal neuron has mixed sensory, motoric and parasympathetic functions. The trigeminal neuron has a large sensory root and a smaller motor root, which sprouts from the side of the pons into three branches as follows: 1) Ophthalmic (CN V1) and 2) Maxillary (CN V2) general sensory components and 3) Mandibular (CN V3) general sensory and branchial motor components. (Rea, P., *Essential Clinical Anatomy of the Nervous System. Ch1: Introduction to the Nervous System.* Elsevier/AP, Academic Press is an imprint of Elsevier: Amsterdam; Boston, 2015; pp 25-27). The trigeminal nerve is in constant communication with the autonomic nervous system, including the ciliary, sphenopalatine, otic, and submaxillary ganglia and the oculomotor, facial, and glossopharyngeal nerves. (Waldman, S. D., *Pain Management E-Book.* 2 ed.; Elsevier Health Sciences: Philadelphia, PA, 2011; pp 1145-1151). In addition, the trigeminal nerve conveys information to key areas in the brain, including the locus coeruleus, the nucleus solitarius, the vagus nerve and the cerebral cortex. The trigeminal nerve also sends signals to the anterior cingulate cortex, which is involved in attention, mood and decision-making.

The following non-limiting examples illustrate exemplary systems and method of use thereof in accordance with various embodiments of the disclosure. The examples are merely illustrative and are not intended to limit the disclosure in any way. While some of the examples are drawn to trigeminal neurons, other nerve cells and electrically active biological cells are contemplated as being stimulated or inhibited with the invention described herein.

Example 1

To investigate whether the activity of a single primary neuron can be evoked by plasmonic and hybrid stimulation, an in-vitro patch-clamp electrical and optical stimulation and recording platform was utilized. Plasmonically evoked APs were recorded in response to laser stimulation with a 50 μm diameter optical fiber (green, 532 nm, 1-5 ms pulses, 50-300 ms overall duration of repetitions, 10 pulses/s). The coating uniformity of the AuNPs coated nanoelectrode surface was verified using scanning electron microscopy (SEM) imaging (FIGS. 1A-C). The colloidal AuNP diameters displayed a normal distribution around 10-20 nm, as shown in transmission electron microscopy (TEM) imaging and in the particle size distribution histogram obtained using a Zetasizer particle counter (FIGS. 1D-E). A visible color change of the gold solution from yellow to reddish maroon was observed during synthesis, and a strong LSPR absorption spectrum using UV-visible spectroscopy had a maximum peak value at the 520 nm wavelength, indicating the formation of AuNPs (FIG. 1F).

Initial neural stimulation experiments were performed to establish a baseline for LSPR-enabled plasmonic stimulation thresholds. All electrophysiological experiments were done in a whole-cell patch-clamp configuration (FIG. 2). The individual trigeminal neurons were patch-clamped in the standard whole-cell current clamp configuration using a patch-clamp electrode and then transiently exposed to a 532 nm laser pulse (100 mW power, 5 ms pulse duration) aimed at the tip of a AuNPs-coated micropipette positioned adjacent (~2 μm in distance) to the patched trigeminal neuron cell (FIG. 2). The holding current was adjusted to the minimum threshold value in order to set the membrane potential to a baseline value (around −70 mV). The trigeminal cells were stimulated with depolarizing electrical currents to trigger a control AP and verify that cells were electrically excitable before proceeding to plasmonic excitation. Then the patch-clamped trigeminal neuron was stimulated with visible 532 nm wavelength light delivered from an optical fiber at 75-125 mW laser power for 1-5 ms duration, by shining the laser beam at the tip of a AuNPs-coated micropipette positioned adjacent (~2 μm in distance) to the patched neuron.

The presence of the AuNPs-coated nanoelectrode, in the close vicinity of the neurons, enabled responses to the applied 75-125 mW, 1-5 ms laser pulses, but with very limited success. A fraction of the stimulated cells (6 out of 23) produced AP responses with pure optical stimulation, while the rest of the cells responded with only a shift in membrane potential or an incomplete/partial repolarization only. Representative traces of the current-clamped trigeminal neurons (N=4), firing action potentials in response to the plasmonic stimulation are presented in FIG. 3A (Middle). It was observed that the pure optical (plasmonic) APs were smaller in magnitude compared to the pure electrical (pre-plasmonic) APs. Also, it was noticeable that the post-plasmonic APs (FIG. 3A-Right), recorded when cells were stimulated with electric current pulses of the same magnitude (150 pA, 300 ms) as in the pre-plasmonic electrical stimulation (FIG. 3A-Left), resulted in APs with significantly smaller amplitude than the original electrical APs. Also, one of the four cells did not survive the plasmonic stimulation; therefore, it could not produce a post-plasmonic electrical AP. Plasmonic action potentials were not consistent, in terms of amplitude and timing, like electrically-induced APs. While laser light between 75-125 mW power was sufficient to reliably trigger APs, two characteristic types of membrane potential outputs were observed.

Type 1 is the characteristic output when the trigeminal neuron cell depolarizes, with no/negligible repolarization of APs following optical laser plasmonic stimulation (FIG. 3B). Approximately 80% of plasmonic stimulation attempts (8 out of 10 cells) resulted in this type of cellular response. This outcome implies cell membrane damage due to plasmonic exposure, or passivation resulting in ion channel dysfunction, which plays a principal role in regulating cellular excitability and whose damage or misbalance can cause irregular depolarization and repolarization patterns. This is manifested in the premature termination or leveling out of the AP response peak, immediately after firing the plasmonic triggered AP discharge, with no/minimal evident repolarization down-slope once reaching the peak. In those cells, the post-plasmonic electrically-evoked AP response typically returned to normal, after a short resting period (few seconds to minutes). In some cases, the post-plasmonic electrical stimulation was not possible, as the cell membrane demonstrated persistently prolonged passive behavior after an optically-induced AP from pure plasmonic stimulation. Similar behavior was reported by researchers who studied effects of AuNPs-aided stimulation of DRG neurons following a laser pulse, indicating cell damage was frequently observed following an AP, resulting in loss of excitability. (Carvalho-de-Souza, J. L.; Treger, J. S.; Dang, B.; Kent, S. B.; Pepperberg, D. R.; Bezanilla, F., Photosensitivity of Neurons Enabled by Cell-Targeted Gold Nanoparticles. *Neuron* 2015, 86, 207-217)

Type 2 is the characteristic output when the cell is partially responsive to optical stimulation right from the start, following a successful pre-plasmonic electrical stimulation AP firing (FIG. 3C). In response to the optical stimulation, cells only produce a very weak membrane potential shift (only 10-20 mV jump), therefore not a complete AP. This can be partially dependent on the nanoelectrode positioning and proximity to the cell (nanoelectrode tip must be next to the cell (<2 µm distance) and laser beam clearly focused on the tip of the nanoelectrode to get sufficient thermal effects in order to produce plasmonic excitation results), as well as the laser power. It was observed that laser power of <75 mW directed at the surface of the AuNPs coated nanoelectrode was insufficient to stimulate the cells. Laser power between 75-125 mW was sufficient to generate the plasmonic effect and evoke AP response in the trigeminal neurons. Some cells (approximately 2 out of 10 cells) had a Type 2 profile of a suppressed membrane potential response when subjected to plasmonic stimulation. These cells recover quickly and are able to fire full AP in response to an electrical stimulation afterwards. Most plasmonic stimulated APs had good depolarization but diminished repolarization peak-to-valley return (~20%) as compared to the original electrically triggered pre-plasmonic APs. This effect lasted, as the diminished repolarization is also noticeable when the cells are electrically stimulated post-plasmonic stimulation. This indicates temporary impairment or permanent irreversible damage of the cell membrane caused by the pure plasmonic stimulation. This side effect is consistent with literature, in that plasmonic stimulation results in a reluctance of the cell to recover quickly and fully to its original base state in a short amount of time once the heating is discontinued. (Carvalho-de-Souza, J. L. et al. 2015; Bazard 2017)

The inventors observed recovery time for the membrane to return to its original pre-plasmonic excitability or resting potential state to be a few seconds to a minute. This could be due to an increased tendency for cellular damage as a consequence of the local photothermal effects, due to high-efficiency light energy accumulation around the gold-nanoparticle-conjugates or due to the gold-nanoparticle-coated nano-surfaces when nanoparticles form large clusters. Quantifying how multiple layers and spatial arrangement of nanoparticles affect the amount of heat generated in the cell's immediate vicinity, as well as further characterizing and optimizing the configuration and uniformity of the nanoparticle-conjugates and coated interfaces to be tailored for optimal neural stimulation may be examined.

Hybrid Stimulation

To address the shortcomings of pure optical stimulation, the inventors conducted experiments with the combination of short-duration optical stimulation pulses and sub-threshold levels of electrical stimulation to avoid damaging the cells. The inventors employed a combined electrical and optical stimulation procedure to utilize the advantages of both stimulation modes, and to introduce the ability to turn on and off individual neurons by fine tuning the proposed hybrid stimulation (combined optical and electrical). The inventors also optimized the neural outputs with various combinations of short duration repetitive bursts of electro-plasmonic pulses to modulate neural firing patterns. The results demonstrate that this type of hybrid electro-plasmonic stimulation can elicit APs in primary neurons, specifically trigeminal neurons.

Representative traces of the current-clamped trigeminal neurons show firing APs in response to the hybrid stimulation when cells were stimulated with the combined 1-5 ms, 532 nm green laser pulses and a sub-threshold electrical current pulses at reduced levels (FIG. 4A-Middle). Observe that the recorded hybrid stimulation APs, when short duration laser pulses (1-5 ms) were combined with electric current pulses, were comparable in magnitude as well as timing to the pure electrical (pre-hybrid) APs. Further, the peak responses recorded with hybrid stimulation were higher than the previously recorded peak responses with pure optical stimulation alone, by 10 to 20 mV. In addition, the post-hybrid APs (FIG. 4A-Right), recorded when cells were stimulated with electric current pulses of the same magnitude (min 150 pA, 5 ms) as in the initial pre-hybrid electrical stimulation (FIG. 4A-Left), resulted in APs with comparable amplitude to the original electrical APs. Also, all cells survived the hybrid stimulation and produced post-hybrid electrical stimulation APs (FIG. 4-Right), unlike post plasmonic stimulation (FIG. 3A-Right). This survival rate was higher as compared to after pure plasmonic stimulation, most likely because there was no membrane damage. It is likely that pairing the short-duration green light pulse stimulus with electrical current pulses aids electrically excitable ion-gate activation in addition to the plasmonically triggered photothermal activation effects. So, these two stimuli have mutually beneficial additive effects on the resulting AP responses.

Figure 5:
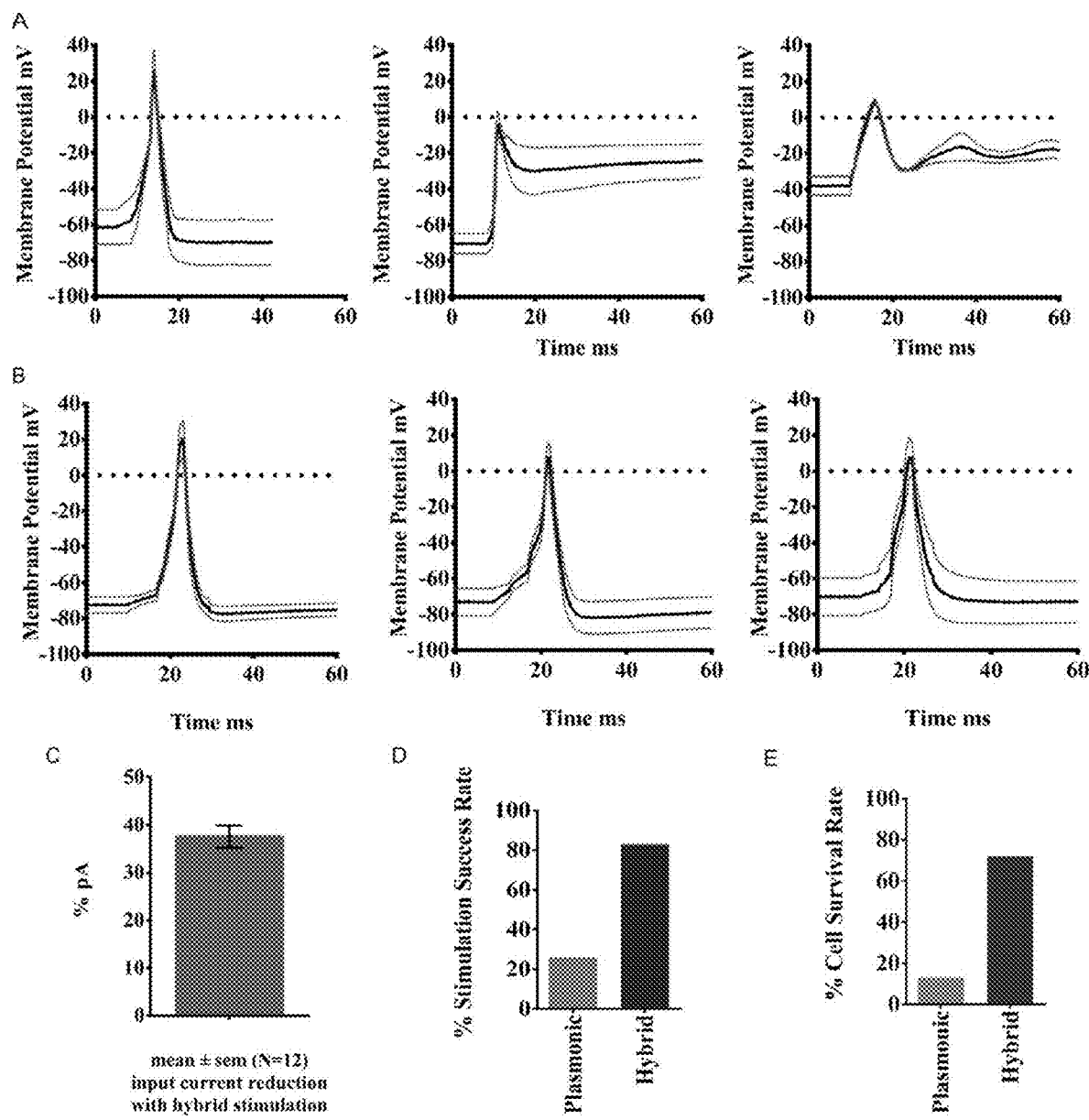

The mean plasmonic AP responses and the mean hybrid (electro-plasmonic) AP responses were further compared for variation and profiling (FIGS. 5A & B). Electrical stimulus amplitude required to evoke APs was reduced by 33-38% when a plasmonic stimulus (1-5 ms pulse width) is added to the electrical input, compared to electrical stimulation alone (FIG. 5C). The inventors also observed that this hybrid neural stimulation has no deleterious effects on the neurons, i.e., the cells fired electrical stimulated APs immediately after the hybrid stimulation, unlike the pure optical stimulation approach alone (reported above). The observed plasmonic vs. hybrid stimulation AP success rates were 26% (N=23) for plasmonic vs. 83% (N=29) for hybrid stimulation of the trigeminal neurons, which equates to 3× the success rate when stimulating with hybrid stimulation vs. plasmonic (FIG. 5D). The observed plasmonic vs. hybrid survival rates were 13% (N=23) post-plasmonic vs. 72% (N=29) of trigeminal neurons post-hybrid Aps, which equates to an order of magnitude >5.5× for survival rate of trigeminal neurons when stimulated with hybrid stimulation compared to plasmonic alone (FIG. 5E).

Further optimization experiments were carried out to study the lead- and lag-time effects of electrical vs. plasmonic pulses in a hybrid electro-plasmonic stimulation combination on AP generation. Electro-plasmonic hybrid stimulation (5 ms; 75-120 mW, 532 nm, 5 ms) pulses were presented to trigeminal neurons at sub-threshold electrical input currents. The inventors found that a lead or lag time greater than 2.0 ms, of either electrical or optical pulse in reference to each other, did not produce regular shaped APs but rather there was only a shift in membrane potentials. As such, a lead or lag time ≤2 ms for either electrical or optical pulse in reference to each other, is needed. Optical leads of up to 0.6 ms before electrical pulses produced standard APs. Electrical lead times of as low as 0.4 ms before optical, and up to 1.4 ms before optical also produced good hybrid APs (FIG. 6A). If delays are >1.4 ms, 100% of the electrical threshold is needed. The inventors concluded that electrical pulse leads of <1 ms before optical was the best condition to excite neurons. For delays up to 1 ms, the radiant exposure necessary for stimulation appears to increase linearly. The inventors found that the greatest benefit was achieved when the stimulations are simultaneous or when the electrical pulse is delivered 0.7 ms to 1.4 ms before the optical pulse.

In additional experiments, the optical pulse duration (1 ms) was fixed and the electrical pulse duration was varied, from 1 to 5 ms, at the hybrid sub-threshold intensity level, where the electrical pulse preceded the optical by 0.7 ms. AP peak responses increased as the sub-threshold electrical pulse duration increased, as shown in a representative hybrid stimulation of a primary trigeminal neuron (FIG. 6B). The difference (delta) between the AP peak value and base value (first minimum after peak) increased with pulse duration increases, due to the increase in the AP peak maxima as well as the increase in the hyperpolarization, resulting in full AP responses for pulses between 3-5 ms in duration.

The findings further show the applicability of short duration pulses (1-5 ms) when applied repeatedly, for sub-threshold electrical and LSPR visible light stimulation pulses, in combination with AuNPs-coated substrates (nano-electrodes), for obtaining repeatable multiple trains of APs from neurons (FIG. 6C). Neural cell survival rates and viability after hybrid stimulation was superior to that of pure optical stimulation. The input current sufficient to trigger APs with multiple hybrid stimulation was up to 40% lower, matching what was observed earlier with single AP recordings. This reinforces the previous findings above, supporting the effectiveness of the proposed platform for hybrid stimulation of neurons.

The inventors have successfully demonstrated a safe and reproducible hybrid laser stimulation of primary trigeminal neurons using single and multiple pulses of visible light and electric currents. This advancement represents an optimized new technology platform for hybrid electro-plasmonic modulation of neuron excitability using visible-light-sensitive gold nanotransducer particles. Gold nanoparticles (AuNPs) were used to coat the plasmonic stimulation nanoelectrodes, since they are known to demonstrate the desired localized surface plasmon resonance (SPR) effects, and are biocompatible in multiple in vivo applications such as drug delivery, bioimaging, biosensors, etc. (Lewinski, N.; Colvin, V.; Drezek, R., Cytotoxicity of Nanoparticles. *Small* 2008, 4, 26-49). LSPR fields are generated as a result of the strong surface interactions between the light and the conduction band electrons of the metal nanoparticles.

The plasmonic oscillations in most metal nanoparticles occur mainly in the ultraviolet (UV) region. However, in the case of gold (Au), silver (Ag), and copper (Cu) nanoparticles, the plasmons shift nearer to the visible light domain, related to electrons in the s-atomic orbitals. Specifically, for gold nanoparticles, used herein, the SPR peak is around 520 nm and it can be tuned with particle size and shape. The AuNPs, especially small size particles (<20 nm), are known to generate localized heating due to SPR, called plasmonic heating. (Coronado, E. A.; Encina, E. R.; Stefani, F. D., Optical Properties of Metallic Nanoparticles: Manipulating Light, Heat and Forces at the Nanoscale. *Nanoscale* 2011, 3, 4042-4059; Huang, X.; El-Sayed, M. A., Gold Nanoparticles: Optical Properties and Implementations in Cancer Diagnosis and Photothermal Therapy. *J. Adv. Res.* 2010, 1, 13-28). The inventors used AuNPs of approximately 20 nm diameter. Visible light at 532 nm, near to the maximum position of the LSPR band in gold, was used to irradiate the AuNPs.

It has been demonstrated that photosensitive AuNPs can be excited upon visible light irradiation and used to wirelessly stimulate primary neurons, and more specifically, trigeminal neurons, without any genetic modifications or direct neural membrane surface contact. Compared to the currently predominant photothermal neuromodulation techniques using direct infrared (IR) laser stimulation, which is susceptible to collateral heating, there is a fundamental difference in transduction. Au nanoparticles are the photoabsorbers, as opposed to water, nearby cells or extracellular fluids, thus allowing heat distribution to be controlled and localized at sub-micron levels. With this approach, biomedical implants based on SPR phenomena have the potential to give better spatial resolution and thus more clinically useful focal stimulation. A hybrid modality is presented here, which adds small amounts of electric currents for cell stimulation, to overcome the issues with reproducibility, repeatability and reliability as seen with pure optical stimulations. Hybrid stimulation significantly reduces the amount of current as compared to pure electrical stimulation (by ~40%) as well as facilitates the firing of multiple APs. Further optimization experiments with different size/shape of gold particles and controlled deposition of layers on different types of nanoelectrodes can further reduce current requirements.

Figure 6:
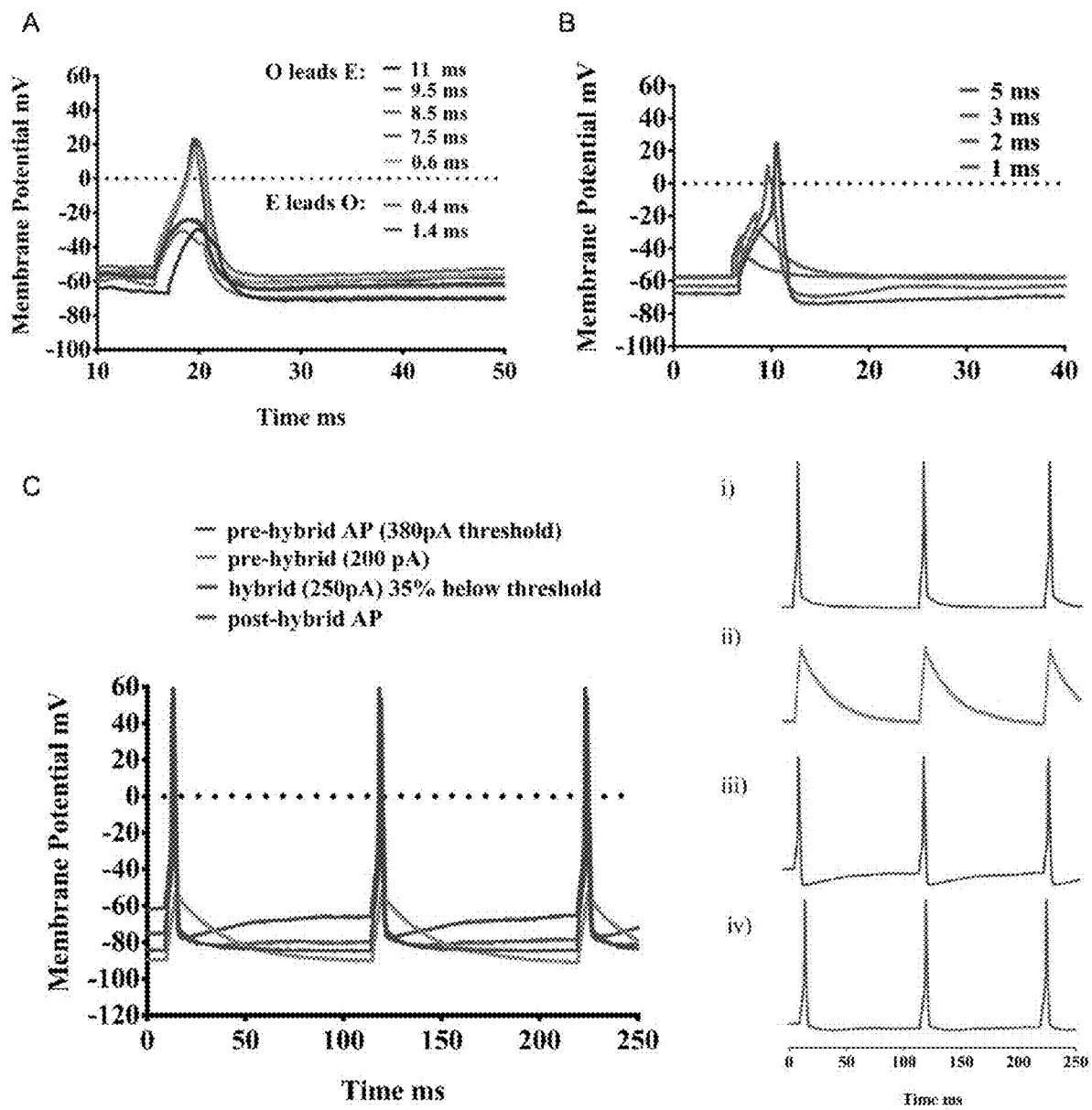

Electro-plasmonic prototypes based on the hybrid neuromodulation modes presented herein have the potential to selectively inhibit or stimulate the electrical excitability of unmodified neurons depending on the specific needs. This can be achieved by varying the tunable electrical and optical stimulation input parameters of the individual inputs through fine-tuning and optimization of the hybrid stimulation parameters (FIG. 6). The fine-tuning of the electro-plasmonic stimulation sequence and variables (lead and lag time, intensity thresholds, duration) administered via short-duration (1-5 ms) repetitive pulsing of both electrical and optical stimuli, allowed for triggering repeatable multiple trains of action potential responses from the stimulated neurons, which is necessary for in-vivo applications. It seems that short moderate power optical pulses in the milliseconds range are necessary for the successful activation of neurons, which is consistent with other studies using nanoparticles.

Relatively high power light is employed by different labs in neuron activation studies (0.31 kW used by Carvalho-de-Souza et al. or 1.5-5 kW used by Migliori et al.), while relatively moderate power light is employed in inhibition studies (15 mW photothermal stimulation intensity used by Yoo et al., or 57 mW used by Martino et al., or 120 mW used by Bazard et al.). (Carvalho-de-Souza, J. L.; Treger, J. S.; Dang, B.; Kent, S. B.; Pepperberg, D. R.; Bezanilla, F., Photosensitivity of Neurons Enabled by Cell-Targeted Gold Nanoparticles. *Neuron* 2015, 86, 207-217; Horikoshi S., Serpone N., Microwaves in Nanoparticle Synthesis: Fundamentals and Applications. In *Microwaves in Nanoparticle Synthesis: Fundamentals and Applications*, Horikoshi S., Serpone N., Ed. John Wiley & Sons: Wiley-VCH Verlag GmbH & Co. KGaA, Boschstr. 12, 69469 Weinheim, Germany, 2013; pp 1-24; Yoo, S.; Hong, S.; Choi, Y.; Park, J. H.; Nam, Y., Photothermal Inhibition of Neural Activity with Near-Infrared-Sensitive Nanotransducers. ACS Nano 2014, 8, 8040-8049; Martino, N.; Feyen, P.; Porro, M.; Bossio, C.; Zucchetti, E.; Ghezzi, D.; Benfenati, F.; Lanzani, G.; Antognazza, M. R., Photothermal Cellular Stimulation in Functional Bio-Polymer Interfaces. Sci. Rep. 2015, 5, 8911; Bazard, P.; Frisina, R. D.; Walton, J. P.; Bhethanabotla, V. R., Nanoparticle-Based Plasmonic Transduction for Modulation of Electrically Excitable Cells. Sci. Rep. 2017, 7, 7803)

Also, a number of infrared neurostimulation (INS) studies reported that short wave infrared (IR) pulses (few milliseconds) can stimulate neural fibers including retinal and cortical neurons, peripheral and cranial nerves, central auditory system even cardiomyocytes and neuroblastoma cells. (Plaksin, M.; Shapira, E.; Kimmel, E.; Shoham, S., Thermal Transients Excite Neurons through Universal Intramembrane Mechanoelectrical Effects. Phys. Rev. X 2018, 8, 011043; Bec, J. M.; Albert, E. S.; Marc, I.; Desmadryl, G.; Travo, C.; Muller, A.; Chabbert, C.; Bardin, F.; Dumas, M., Characteristics of Laser Stimulation by Near-Infrared Pulses of Retinal and Vestibular Primary Neurons. Lasers Surg. Med. 2012, 44, 736-745; Cayce, J. M.; Friedman, R. M.; Chen, G.; Jansen, E. D.; Mahadevan-Jansen, A.; Roe, A. W., Infrared Neural Stimulation of Primary Visual Cortex in Non-Human Primates. NeuroImage 2014, 84, 181-190; Cayce, J. M.; Friedman, R. M.; Jansen, E. D.; Mahavaden-Jansen, A.; Roe, A. W., Pulsed Infrared Light Alters Neural Activity in Rat Somatosensory Cortex In Vivo. NeuroImage 2011, 57, 155-166; Wells, J.; Kao, C.; Mariappan, K.; Albea, J.; Jansen, E. D.; Konrad, P.; Mahadevan-Jansen, A., Optical Stimulation of Neural Tissue In Vivo. Opt. Lett. 2005, 30, 504-506; Wells, J.; Kao, C.; Konrad, P.; Milner, T.; Kim, J.; Mahadevan-Jansen, A.; Jansen, E. D., Biophysical Mechanisms of Transient Optical Stimulation of Peripheral Nerve. Biophys. J. 2007, 93, 2567-2580; Izzo, A. D.; Richter, C. P.; Jansen, E. D.; Walsh Jr, J. T., Laser Stimulation of the Auditory Nerve. Lasers Surg. Med. 2006, 38, 745-753; Littlefield, P. D.; Vujanovic, I.; Mundi, J.; Matic, A. I.; Richter, C. P., Laser Stimulation of Single Auditory Nerve Fibers. The Laryngoscope 2010, 120, 2071-2082 Teudt, I. U.; Nevel, A. E.; Izzo, A. D.; Walsh Jr, J. T.; Richter, C. P., Optical Stimulation of the Facial Nerve: A New Monitoring Technique? The Laryngoscope 2007, 117, 1641-1647; Izzo, A. D.; Walsh Jr, J. T.; Ralph, H.; Webb, J.; Bendett, M.; Wells, J.; Richter, C. -P., Laser Stimulation of Auditory Neurons: Effect of Shorter Pulse Duration and Penetration Depth. Biophys. J. 2008, 94, 3159-3166; Richter, C. -P.; Rajguru, S. M.; Matic, A. I.; Moreno, E. L.; Fishman, A. J.; Robinson, A. M.; Suh, E.; Walsh Jr, J. T., Spread of Cochlear Excitation During Stimulation with Pulsed Infrared Radiation: Inferior Colliculus Measurements. J. Neural Eng. 2011, 8, 056006; Rajguru, S. M.; Richter, C. P.; Matic, A. I.; Holstein, G. R.; Highstein, S. M.; Dittami, G. M.; Rabbitt, R. D., Infrared Photostimulation of the Crista Ampullaris. J. Physiol. 2011, 589, 1283-1294; Bazard, P.; Frisina, R. D.; Walton, J. P.; Bhethanabotla, V. R., Nanoparticle-Based Plasmonic Transduction for Modulation of Electrically Excitable Cells. Sci. Rep. 2017, 7, 7803)

It has been reported that INS is mediated by rapid temperature transients induced by surroundings absorption and that such transients can be induced with other types of photo-absorption as well, thus with visible light plasmonic stimulation as used herein. (Shapiro, M. G.; Homma, K.; Villarreal, S.; Richter, C. -P.; Bezanilla, F., Infrared Light Excites Cells by Changing Their Electrical Capacitance. Nat. Commun. 2012, 3, 736; Wells, J.; Kao, C.; Konrad, P.; Milner, T.; Kim, J.; Mahadevan-Jansen, A.; Jansen, E. D., Biophysical Mechanisms of Transient Optical Stimulation of Peripheral Nerve. Biophys. J. 2007, 93, 2567-2580; Farah, N.; Brosh, I.; Butson, C. R.; Shoham, S., Photo-Thermal Neural Excitation by Extrinsic and Intrinsic Absorbers: A Temperature-Rate Model. 2012, Neurons and Cognition). It has been previously shown that the rapid temperature transients are directly accompanied by changes in cell membrane capacitance and mechanoelectric properties and resulting modulation of ionic membrane currents can lead to cell stimulation. (Plaksin, M.; Shapira, E.; Kimmel, E.; Shoham, S., Thermal Transients Excite Neurons through Universal Intramembrane Mechanoelectrical Effects. Phys. Rev. X 2018, 8, 011043). However, most previous optical/laser studies showed inhibition/modulation of spontaneous neural or cardiac activity; rather than excitation.

In contrast, the inventors show that exciting neurons is feasible with the hybrid stimulation approach. Furthermore, studies have been conducted using external photoresponsive materials such as gold nanoparticles, some needing genetic modification of the targeted cell, as mentioned above. Other approaches where plasma-membrane-targeted gold nanorods (pm-AuNRs) are prepared with a cationic protein/lipid complex to activate the thermosensitive cation channel, TRPV1, in intact neuronal cells have been tried.[20] The latter method provides an optogenetic platform without the need for prior genetic engineering of the target cells. In contrast, here the inventors use AuNPs coated on an external microelectrode which does not need any bio-conjugation or surface modification of the nano-neural interface to achieve the triggering of neural stimulation. Inhibition or activation is controlled by fine tuning the hybrid input stimuli.

Materials and Methods

Gold Nanoelectrode Fabrication for Neuron Stimulation. The first-generation AuNP coated nanoelectrode system consisted of approximately 20 nm diameter colloidal AuNPs coated onto the surface of a glass micropipette, as reported in the inventors' previous work, herein incorporated by reference into this disclosure. (Bazard et al. 2017). Briefly, colloidal AuNPs (spheres) were synthesized by a citrate method[22, 45-48] that involves reduction of a gold salt solution (Chloroauric acid $HAuCl_4 \cdot 3H_2O$) by sodium citrate ($Na_3C_6H_5O_7 \cdot 2H_2O$) aqueous solution. Spherical AuNPs with 20 nm diameter were chosen because they are easily made with limited size dispersion into a colloidal solution and are generally considered to be biocompatible. (Shukla, R.; Bansal, V.; Chaudhary, M.; Basu, A.; Bhonde, R. R.; Sastry, M., Biocompatibility of Gold Nanoparticles and Their Endocytotic Fate Inside the Cellular Compartment: A Microscopic Overview. Langmuir 2005, 21, 10644-10654). The method followed was the one described by Nath & Chilkoti who studied the interaction of a biomolecule with a monolayer of AuNPs coated glass cover-slips. (Nath, N.; Chilkoti, A., A Colorimetric Gold Nanoparticle Sensor to Interrogate Biomolecular Interactions in Real Time on a Surface. Anal. Chem. 2002, 74, 504-509). The micropipette coating procedure involved three steps: 1) cleaning the glass surface, 2) functionalization of the glass surface with γ-(aminopropyl) triethoxysilane, and 3) coating of the functionalized glass surface with colloidal AuNPs. The inventors used this method in a similar manner for the current study to coat the synthesized AuNPs onto the borosilicate nanoelectrodes, with prior silanization of the glass pipettes surface using 10% volume solution of γ-(aminopropyl) triethoxysilane) (APTES) in ethanol. The silanized glass electrodes were dipped overnight at room temperature in the synthesized colloidal AuNPs suspension, resulting in a self-arranged chemical deposition of AuNPs coating onto the tip surface of the microelectrodes, which possess plasmonic properties.

Primary Neuron Cell Culture. Trigeminal neurons were obtained from the brain of 5-7 week old C57B1/6 mice. The trigeminal neurons were removed after decapitation and maintained in a cold (4-5° C.) $Ca^{2+}$- and $Mg^{2+}$-free Hanks' balanced salt solution (HBSS; Gibco BRL, Rockville, MD, USA). Trigeminal neurons were dissociated enzymatically with HBSS containing collagenase type IA (1 mg ml-1, Sigma, St Louis, MO, USA) and dispase II (1 mg ml-1, Boehringer Mannheim, Mannheim, Germany). Enzymes, collagenase type 1 and dispase II (2 mg/ml), were dissolved in HBSS and sterile filtered using a white PVDF syringe filter before use. The required solutions were prepared, 40 ml of HBSS, 21 ml of L15+10% FBS, and 11 ml L15+FBS. The tubes of L15 were placed in the incubator at 37° C., 5% $CO_2$ to warm up. Meanwhile, a 20-40 g mouse was euthanized using $CO_2$ overdose, decapitated and the trigeminal nerves dissected out. The trigeminal ganglia were minced into pieces and left to incubate at 37° C. in the collagenase/dispase II solution for 50 min. During this incubation, coated coverslips were transferred to a 6-well plate. Coverslips were cleaned in 100% ethanol and then coated with a 5 µg/ml laminin mixed in poly-d-lysine (PDL) coating solution. Coverslips were left at room temp for at least 30 min. Then, the coating solution was aspirated with a pipette, and the coverslips washed with 200 µl of sterile deionized (DI) water and allowed to dry before use. The Bunsen burner was set, and three glass pipettes were fire polished for trituration—large, medium (10-15 sec to take up solution), and small (45-60 sec to take up solution) size bores. After 30 min of incubation, the neurons are triturated with the wide bore pipette, and then put back into the 37° C. water bath for another 20 min. Finally, they were dissociated with the medium followed by the small-bore pipette. The cell suspension was then, centrifuged at 2200 rpm for 2 min. A 55 µl of pen/strep solution (1:200) was added to the 11 ml of L15+FBS previously left in 37° C. incubator. Next, the HBSS was aspirated and pellet was re-suspended in 10 ml L-15 medium containing 10% FBS and centrifuged again (2200 rpm, 2 min). Medium was aspirated again, and cells were re-suspended in 10 ml L-15 medium containing 10% FBS and pen/strep and then centrifuged again (700 g, 2 min). Finally, the medium was aspirated, and cells were re-suspended in 100 µl L15+FBS+pen/strep (20 µl per coverslip). Suspension was pipette mixed 50 times with a p200 pipette and transferred in portions of 20 µl suspension to coverslips coated with PDL and laminin. The 6-well plate (culture dishes) was placed in incubator for 1-2 hr to incubate. Then, the wells were toped (flooded) with 2 ml of L15 containing 10% FBS and left to incubate at 37° C. All cells were used within 36 h.

Plasmonic and Hybrid Optical Stimulation Method. For plasmonic and hybrid stimulations, the Au nanoparticles coated nanoelectrode was placed adjacent (2 µm) to the cell, while the cell is patched in whole cell current clamp configuration using a micropipette equipped to measure the plasmonic responses. The 532 nm green laser (OBIS 532 nm laser, Coherent, Santa Clara, CA) pulses were focused on the tip of the AuNPs-coated nanoelectrode through an optical fiber with a 50 µm inside diameter (custom fiber optic cannula from ThorLabs). Electrical evoked action potentials were measured pre and post optical stimulation. For hybrid stimulation, electrical stimulus was added in addition to the optical stimulus. Cellular response was recorded using the patch clamp system in whole-cell current-clamp configuration mode.

Whole-cell patch-clamp technique. Whole cell patch-clamp technique was used in conjunction with a Multiclamp 700B amplifier and Digidata 1440 data acquisition interface system (Molecular Devices, Sunnyvale, CA), and pCLAMP-9 software (Axon Instruments, Union City, CA, USA). The patch-clamp borosilicate pipette, having resistance 4-7 MΩ, was filled with an intracellular solution, using a micro syringe. The micropipettes used for the patch-clamp recordings were pulled using a glass micropipette puller (P-97, from Sutter Instruments, Novato, CA) by adjusting the pulling parameters to obtain 4-7 MΩ pipette resistance. (Oesterle, A., Pipette Cookbook 2018: P-97 & P-1000 Micropipette Pullers. In *Sutter Instrument Company* [Online]; Oesterle, A., Ed. Novato, CA, 2015; pp 5-33). The pipette tip is placed in the bath filled with extracellular solution and the tip focused under 20× magnification. To form a gigaseal, a small voltage pulse is applied; 10 mV, 50 ms and current responses recorded. The pipette is slowly lowered down. When very near to the cell, the movement is stopped, the pipette potential is zeroed, and a little suction applied as needed to patch the cell and form Giga-seal (resistance>1 G-Ohm). A membrane break-through was attempted by applying pressure to achieve the whole cell configuration.

Extracellular Solution (ECS). Extracellular solution, used to flood the cells in the dish, was prepared with the following composition (mM): 154 NaCl; 4.7 KCl; 1.2 $MgCl_2$; 2.5 $CaCl_2$; 10 N-[2-hydroxyethyl]piperazine-N'-[2-ethanesulphonic acid] (HEPES); pH adjusted between 7.3 and 7.5 with NaOH.

Intracellular Solution (ICS). Patch pipettes (4-7 MΩ) were filled with an intracellular solution (mM): 140 KCl, 1 $CaCl_2$, 2 $MgCl_2$, 10 N-[2-hydroxyethyl]piperazine-N'-[2-ethanesulphonic acid] (HEPES), 10 (D(+)-Glucose, reagent ACS, Anhydrous), 11 ethylene glycol-bis((β-aminoethyl ether)-N,N,N',N'-tetraacetic acid (EGTA); pH 7.3 adjusted with KOH. In current-clamp mode, holding membrane potential was maintained at −60 to −70 mV. Threshold (TH, the most hyperpolarized potential at which the cell was able to fire an AP) was determined by injecting increments of depolarizing current (Δ of 50-100 pA) for 5 ms pulse width, until the cell started to elicit AP.

All the animal protocols and procedures were approved by the University of South Florida Institutional Animal Care and Use Committee (IACUC) and are consistent with US Federal and NIH guidelines, with the necessary training provided. The mouse tissue was provided by the laboratory of Prof. Tom Taylor-Clark, College of Medicine Molecular Pharmacology & Physiology, University of South Florida, Tampa, FL.

Conclusion

In summary, the inventors demonstrated that a reduction of up to ~40% of the input current threshold can be achieved for triggering APs. Cells stay healthy longer after repeated exposure to the hybrid stimulation platform, with a survival rate greater than five times as compared to pure plasmonic/optical stimulation. In addition, the cell's stimulation success rate was three times greater with the hybrid stimulation. The inventors have shown that combining short-duration green visible light optical pulses with the complementary sub-threshold level electric current pulses can reliably trigger a train of action potentials, possibly by activating ion channels in patterns like standard APs. Collectively, the combined hybrid stimulation input produced reliable APs related to more favorable membrane hyperpolarization. Nanomaterials, specifically gold, maximize the utility of thermal stimulation via surface plasmon resonance phenomena. The use of nanotechnology as a medium for photothermal stimulation has the potential to make way for non-invasive neural stimulators capable of cell-specific targeting, allowing for improved restoration of sensorimotor functions and removing side effects exhibited with current neuromodulation methods. Nanomaterials-enabled plasmonic stimulation, when paired with sub-threshold electrical stimulation inputs in a tunable hybrid neuromodulation mode, can revolutionize the way neural or cardiac stimulation therapy is performed.

Example 2—Tunable Cochlear Implants (Prophetic)

A hybrid modulation neurodevice based on non-contact and non-modification of neural interface approaches, using wireless SPR phenomena, is the ultimate solution for achieving enhanced spatial resolution and thus, more clinically useful focal stimulation of neurons. It has the additional advantage of not generating excessive electrical artifacts that could interfere with concurrent neurophysiological recordings, currently used in electrical closed-loop neuroprosthetic systems for treating brain disease, hearing loss/deafness, and similar neurological disorders, as well as in experimental neuroscience.

After more than five decades, cochlear implant technology still relies on electrical stimulation of the auditory nerves. Some of the latest advances in cochlear technology are based on bimodal solutions involving a cochlear implant and a hearing aid working together to give the patient a more natural hearing experience rather than just the traditional hearing aid or cochlear implant used alone. (Dorman, M. F.; Gifford, R. H.; Spahr, A. J.; McKarns, S. A., The Benefits of Combining Acoustic and Electric Stimulation for the Recognition of Speech, Voice and Melodies. *Audiol. Neurotol*, 2008, 13, 105-112; Wolfe, J.; Morals, M.; Schafer, E., Speech Recognition of Bimodal Cochlear Implant Recipients Using a Wireless Audio Streaming Accessory for the Telephone. *Otol. Neurotol.* 2016, 37, e20-e25). However, this bimodal solution does not address the underlying cause for why cochlear implant users have difficulty hearing speech in background noise and suffer from poor music perception.

A new generation of high-acuity neural modulation prosthetic devices, tunable for the individual patient's needs, are developed using the hybrid neurostimulation methods discussed in Example 1, which utilize visible light for electroplasmonic stimulation. Such devices are superior to traditional electrical stimulation technologies as well as newer photothermal or optogenetic technologies which use infrared or NIR light. Specifically, cochlear implants that offer improved frequency specificity with more selective, focused and tunable activation of the auditory neurons along the cochlear frequency axis in deaf patients are developed. These advances are used for implementation of more physiologically effective stimulation channels to achieve better encoding of complex sounds in the auditory nerve via improved spatial resolution.

The hybrid stimulation approach allows the auditory nerve to be stimulated with lower current levels while improving specificity, success rate and survival rate of the stimulated neurons, thereby increasing battery life of the cochlear implants. The new generation hybrid cochlear implant technology may be comprised of an array of optical fibers (~50 μm diameter), or similar optical conduit media such as waveguides (~50×80 μm individual cross section area), sorted in a linear or twisted bundle arrangement (~800 μm overall diameter). This array of optical fibers or optical conduit media pairs with an existing technology electrical stimulation electrode array (typically a series of tiny metal rings, as currently used by cochlear implant manufacturers). The optical fibers and electrical stimulation electrode array are used as a pair to form a hybrid electro-optical or electro-plasmonic cochlear implant for hybrid electro-plasmonic stimulation of the auditory nerve.

Structurally, an optical array of waveguide fibers are added alongside the existing electrode array such that they are aligned at the distal end of the cochlear implant. This optical array matches the number of electrode rings (for instance, 24 waveguides to pair with 24 electrode rings) and are staggered in such a way to allow each optical distal end to pair with a metal ring from the electrode array until all optical fiber ends and electrode rings are paired. The important detail being, each optical fiber, i.e. waveguide, has an AuNPs coating applied or built in at the distal end and positioned to protrude alongside the metal rings of the electrode array, therefore forming an electro-optical array of electrode-waveguide pairs arranged in an alternating fashion for the best hybrid stimulation access to the auditory nerve. The proposed hybrid neurostimulation methodology and device prototype, based on the research findings presented herein, provides major invention contribution for any future next generation cochlear implants and sound modulation technology.

Example 3—Myography Stimulators and Methods of Use (Prophetic)

Other neurostimulation applications are also considered including, but not limited to, Myography stimulators. The Myography stimulators can be designed to implement the hybrid electro-plasmonic methodology for stimulation and treatment of peripheral neuropathy as an alternative to current electromyography.

Electromyography (EMG) generally measures muscle response or electrical activity in response to a nerve's stimulation of muscle. In general, a small needle electrode is inserted into different muscles to stimulate the muscle fibers. Electrical activity is measured when the muscle contracts and relaxes. The hybrid neurostimulation technology described herein can be used to replace the electrode with a hybrid device capable of both electrical and optical stimulation.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of modulating neural activity in at least one neuron comprising:
   delivering an electrical pulse at a sub-threshold level, lasting between about 1-10 ms, to the at least one neuron using a nanoelectrode coated in an array of gold nanoparticles and positioned adjacent to the at least one neuron; and delivering an optical pulse, lasting between about 1-5 ms, to the at least one neuron;

wherein at least one action potential of the at least one neuron is stimulated or inhibited by the delivery of the electrical pulse and the optical pulse to modulate the neural activity.

2. The method of claim 1, further comprising delivering subsequent pulses in an alternating pattern of one electrical pulse and one optical pulse to the at least one neuron.

3. The method of claim 1, further comprising delivering subsequent optical and electrical pulses simultaneously.

4. The method of claim 1, further comprising adjusting variables comprising sequence, lead and lag time, intensity thresholds, duration, or a combination thereof to fine-tune the stimulation or inhibition of the at least one action potential of the at least one neuron.

5. The method of claim 1, wherein time between the electrical pulse and the optical pulse is between about 0.5 ms to 2 ms.

6. The method of claim 1, wherein the array of gold nanoparticles are configured to produce plasmonic heating when excited by a wavelength of light near their surface plasmon resonance peak.

7. The method of claim 6, wherein the wavelength of light is between about 380 nm to about 800 nm.

8. The method of claim 6, wherein the wavelength of light is about 532 nm.

9. A method of stimulating or inhibiting an action potential in at least one nerve cell comprising:

positioning a gold nanoparticles-coated nanoelectrode adjacent to the at least one nerve cell;

delivering an electrical pulse at a sub-threshold level, lasting between about 1 to 10 ms, to the at least one nerve cell;

delivering an optical pulse, lasting between about 1 to 5 ms, to the at least one nerve cell; and wherein the action potential of the at least one nerve cell is stimulated or inhibited by the delivery of the electrical pulse and the optical pulse.

10. The method of claim 9, further comprising delivering subsequent pulses in an alternating pattern of one electrical pulse and one optical pulse wherein time between the electrical pulse and the optical pulse is between about 0.5 ms to 2 ms.

11. The method of claim 9, further comprising delivering the optical pulse and the electrical pulse simultaneously.

12. The method of claim 9, further comprising adjusting variables comprising sequence, lead and lag time, intensity thresholds, duration, or a combination thereof to fine-tune the stimulation or inhibition of the action potential of the at least one nerve cell.

13. The method of claim 9, wherein the gold nanoparticles are configured to produce plasmonic heating when excited by a wavelength of light near their surface plasmon resonance peak.

14. The method of claim 13, wherein the wavelength of light is between about 380 nm to about 800 nm.

15. The method of claim 13, wherein the wavelength of light is about 532 nm.

16. A method of stimulating multiple action potentials in a nerve cell comprising:

positioning a gold nanoparticles-coated nanoelectrode adjacent to the at least one nerve cell; and delivering alternating optical and sub-threshold level electrical pulses to the at least one nerve cell;

wherein the optical pulses have a pulse width between about 1 to 5 ms;

wherein the electrical pulses have a pulse width between about 1 to 10 ms;

wherein the time period between each of the optical and each of the electrical pulses is between about 0.5 ms to 2 ms.

17. The method of claim 16, further comprising adjusting variables comprising sequence, lead and lag time, intensity thresholds, duration, or a combination thereof to fine-tune the stimulation of the multiple action potentials of the at least one nerve cell.

18. The method of claim 16, wherein the gold nanoparticles are configured to produce plasmonic heating when excited by a wavelength of light near their surface plasmon resonance peak.

\* \* \* \* \*